(12) United States Patent
Strachan et al.

(10) Patent No.: US 8,918,152 B2
(45) Date of Patent: Dec. 23, 2014

(54) PARALLEL FABRICATION OF NANOGAPS AND DEVICES THEREOF

(75) Inventors: Douglas R. Strachan, Lexington, KY (US); Danvers E. Johnston, Berwyn, PA (US); Beth S. Guiton, Philadelphia, PA (US); Peter K. Davies, Newtown, PA (US); Dawn A. Bonnell, West Chester, PA (US); Alan T. Johnson, Jr., Philadelphia, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 1128 days.

(21) Appl. No.: 12/526,710

(22) PCT Filed: Feb. 13, 2008

(86) PCT No.: PCT/US2008/053793
§ 371 (c)(1),
(2), (4) Date: Feb. 16, 2010

(87) PCT Pub. No.: WO2008/121445
PCT Pub. Date: Oct. 9, 2008

(65) Prior Publication Data
US 2010/0144535 A1 Jun. 10, 2010

Related U.S. Application Data

(60) Provisional application No. 60/901,360, filed on Feb. 13, 2007, provisional application No. 60/954,884, filed on Aug. 9, 2007.

(51) Int. Cl.
*H01B 1/00* (2006.01)
*H01L 39/24* (2006.01)
*H01L 43/12* (2006.01)
*H01L 21/44* (2006.01)
*B81C 1/00* (2006.01)
*G01N 21/55* (2014.01)

(52) U.S. Cl.
CPC ........ *H01L 39/2467* (2013.01); *B81C 1/00126* (2013.01); *H01L 43/12* (2013.01); *G01N 21/554* (2013.01)
USPC ........... 505/220; 505/470; 505/100; 438/658; 438/669; 438/674; 257/414

(58) Field of Classification Search
USPC .......... 505/100, 220, 300, 470, 818; 252/500; 438/49, 57; 257/E31.052, 414; 977/700, 742, 932
See application file for complete search history.

(56) References Cited

U.S. PATENT DOCUMENTS

| | | | |
|---|---|---|---|
| 5,751,156 A | * | 5/1998 | Muller et al. ................. 324/699 |
| 7,030,452 B2 | | 4/2006 | Tao et al. |
| 2003/0089899 A1 | | 5/2003 | Lieber et al. |

FOREIGN PATENT DOCUMENTS

| WO | WO 2006/101292 | * | 9/2006 | .............. H01L 21/00 |
|---|---|---|---|---|
| WO | WO 2006/102292 A2 | | 9/2006 | |

OTHER PUBLICATIONS

Dong et. al., "Using noise for controlled disassembly of nanoscale gold wires," Nanotechnology 17 (2006) 5124-5130.*

(Continued)

*Primary Examiner* — Stanley Silverman
*Assistant Examiner* — Kallambella Vijayakumar
(74) *Attorney, Agent, or Firm* — Baker & Hostetler LLP

(57) ABSTRACT

Disclosed are devices comprising multiple nanogaps having a separation of less than about 5 nm. Also disclosed are methods for fabricating these devices.

22 Claims, 17 Drawing Sheets

(56) References Cited

OTHER PUBLICATIONS

Strachan et al, "Clean Electromigrated Nanogaps Imaged by Transmission Electron Microscopy," Nano Letters, 2006 vol. 6, No. 3, pp. 441-444, (on Line Published : Jan. 26, 2006).*

Shih et al, Nanometer Gaps by Feedback-Controlled Electromigration,"The 12th tnternalionel Conference on Solid State Sensors, Actualors and Microsystems," Boston, Jun. 8-12, 2003, IEEE, 3E91.P, pp. 1530-1533.*

Strachan et al, "Controlled fabrication of nanogaps in ambient environment for molecular electronics," Applied Physics Letters 86, 043109, 2005.*

Muller et al., "Conductance and Supercurrent Discontinuities in Atomic-Scale Metallic Constrictions of Variable Width", Phys. Rev. Lett., Jul. 6, 1992, 69, (1), 140-143.

Bolotin et al., "From Ballistic Transport to Tunneling in Electromigrated Ferromagnetic Breakjunctions", Nano Lett., Jan. 2006, 6, (1), 123-127.

Qi et al., "Miniature Organic Transistors with Carbon Nanotubes as Quasi-One-Dimensional Electrodes", J. Am. Chem. Soc., Sep. 29, 2004, 126, (38), 11774-11775.

Guo et al., "Covalently Bridging Gaps in Single-Walled Carbon Nanotubes with Conducting Molecules", Science, Jan. 20, 2006, 311, (5759), 356-359.

Discussion contained in Prof. Walter F. Smith's web page http://www.haverford.edu/physics-astro/Smith/#Single%20Electron%20Tunneling, Last Updated Dec. 30, 2008.

Atay et al., "Strongly Interacting Plasmon Nanoparticle Pairs: From Dipole-Dipole Interaction to Conductively Coupled Regime", Nano Lett., Sep. 2004, 4, (9), 1627-1631, EPUB: Aug. 12, 2004.

Dadosh et al., "Measurement of the Conductance of Single Conjugated Molecules", Nature, Aug. 4, 2005, 436, 677-680.

Danckwerts et al., "Optical Frequency Mixing at Coupled Gold Nanoparticles", Phys. Rev. Lett., Jan. 12, 2007, 98, (2), 026104-1-026104-4, EPUB: Jan. 10, 2007.

Esen et al., "Temperature Control of Electromigration to Form Gold Nanogap Junctions", Appl. Phys. Lett., Dec. 19, 2005, 87, (26), 263101-1-263101-3.

Grigorenko et al., "Nanofabricated Media With Negative Permeability at Visible Frequencies", Nature, Nov. 17, 2005, 438, 335-338.

Hadeed et al., "Controlled Fabrication of 1-2 nm Nanogaps by Electromigration in Gold and Gold-Palladium Nanowires", Appl. Phys. Lett., Sep. 21, 2007, 91, (12), 123120-1-123120-3.

Tamaru et al., "Resonant Light Scattering From Individual Ag Nanoparticles and Particle Pairs", Appl. Phys. Lett., Mar. 11, 2002, 80, (10), 1826-1828.

Xu et al., "Electromagnetic Contributions to Single-Molecule Sensitivity in Surface-Enhanced Raman Scattering", Phys. Rev. E., Sep. 2000, 62, (3 part B), 4318-4324.

Lalayan et al., "Anomalous Field Enhancement From the Superfocusing of Surface Plasmons at Contacting Silver Surfaces", J. Appl. Phys., 2002, 91, 5, 2965-2968.

Maier et al., "Plasmonics—A Route to Nanoscale Optical Devices", Adv. Mater., 2001, 13, (19), Oct. 2, 2001, 1501-1505.

Maier et al., "Local Detection of Electromagnetic Energy Transport Below the Diffraction limit in Metal Nanoparticle Plasmon Waveguides", Nature Materials, Apr. 2003, 2, (4), 229-232.

Pasupathy et al., "The Kondo Effect in the Presence of Ferromagnetism", Science, Oct. 1, 2004, 306, 86-89.

Strachan et al., "Controlled Fabrication of Nanogaps in Ambient Environment for Molecular Electronics", Appl. Phys. Lett., Jan. 21, 2005, 86, 043109-1-043109-3.

Ward et al., "Electromigrated Nanoscale Gaps for Surface-Enhanced Raman Spectroscopy", Nano Lett., Epub Apr. 13, 2007, May 2007, 7, (5), 1396-1400.

Geim et al., "The Rise of Graphene", Nature Materials, Mar. 2007, 6, (3), 183-191.

Dong et al., "Using noise for controlled disassembly of nanoscale gold wires." Nanotechnology Sep. 22, 2006, vol. 17, 5124-5130. (abstract) [online] [retrieved on Sep. 9, 2008]. Retrieved from the Internet: URL: http:/lwww.iop.org/EJ/article10957-448411712010141nano6~20~014.pdf.

Mahapatro et al., "Nanometer Scale Electrode Separation (Nanogap) Using Electromigration at Room Temperature," IEEE Transactions on Nanotechnology, May 2006, 5, (3), 232-236.

Shih et al., "Nanometer Gaps by Feedback-Controlled Electromigration," Transducers, '03. $12^{th}$ Int'l. Conf. on Solid-State Sensors, Actuators and Microsystems. Digest of Technical Papers (Cat. No. 03TH8664), Jun. 8-12, 2003, 1530-1533.

Trouwborst et al., "The Role of Joule Heating in the Formation of Nanogaps by Electromigration", J. Appl. Phys., 2006, 99, 114316, 1-7.

Worne et al., "Electronic transport of low concentrations of P3HT molecules across nanogap source-drain electrodes" American Physical Society March Meeting, Mar. 5-9, 2007, Denver, CO, 52, (1) Session Y26.00006 12:39pm—Abstract Only.

* cited by examiner

US 8,918,152 B2

PARALLEL FABRICATION OF NANOGAPS AND DEVICES THEREOF

CROSS-REFERENCE TO RELATED APPLICATIONS

This application is the National Stage of International Application No. PCT/US2008/053793, filed Feb. 13, 2008, which claims the benefit of U.S. Pat. App. Ser. No. 60/901,360, filed Feb. 13, 2007, and U.S. Pat. App. Ser. No. 60/954,884, filed Aug. 9, 2007, the entirety of which applications is incorporated by reference herein.

STATEMENT OF GOVERNMENT INTEREST

The Government may have certain rights in the present invention. Research related to the present invention was supported by National Science Foundation, Nanoscale Science and Engineering Center, Department of Materials Research grant NSF NSEC DMR 0425780, and by National Science Foundation, Nanoscale Interdisciplinary Research Team grant NSF-NIRT 0304531.

FIELD OF THE INVENTION

The present invention pertains to the field of materials science. The present invention also pertains to the field of nano-scale electronic devices.

BACKGROUND OF THE INVENTION

Various scientific and patent publications are referred to herein. Each is incorporated by reference in its entirety.

Nanoscale gaps have application in circuits, transistors, chemical sensors, magnetic-spin valves, Josephson junctions, and bolometers. However, development of a reliable, reproducible fabrication process for nanoscale gaps ("nanogaps") useful as contact electrodes is one of the major technological challenges faced in the development of molecular electronics.

While a number of approaches for fabricating such nanogaps have been advanced in recent years, there remains no viable method for fabricating a plurality of nanogaps with separations less than about 5 nm regime for producing integrated molecular circuits. Parallel production of such nanogaps would enable their use in applications requiring mass-produced devices. Accordingly, there is a need in the field for methods for producing nanogaps having separations of less than about 5 nm, ideally with high reproducibility.

SUMMARY OF THE INVENTION

Disclosed are methods for fabricating a plurality of nanogaps, comprising controllably applying a voltage across a plurality of constrictions residing in a conductive material comprising a plurality of ions, the constrictions being placed in electrical communication with one another by a conductive material, the electrical resistance between neighboring constrictions being less than the electrical resistance across a constriction, the controllably applied voltage giving rise to heating within the constrictions, the heating within the constrictions giving rise to nanogaps comprising at least two opposing faces, and the mean distance between the opposing faces of the nanogaps being less than about 5 nm.

Also disclosed are devices, comprising a plurality of nanogaps formed in a first conductive material, the nanogaps comprising opposing electrodes, the opposing electrodes being separated by less than about 5 nm, the opposing electrodes comprising faces, and the faces of the opposing electrodes being essentially crystalline.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 6a shows constrictions formed from a first material and connected by a second material, FIG. 6b shows the nanogaps formed by electromigration within the constrictions, and FIG. 6c shows the separated nanogaps following removal of the second material;

DETAILED DESCRIPTION OF ILLUSTRATIVE EMBODIMENTS

Terms

Figure 1:
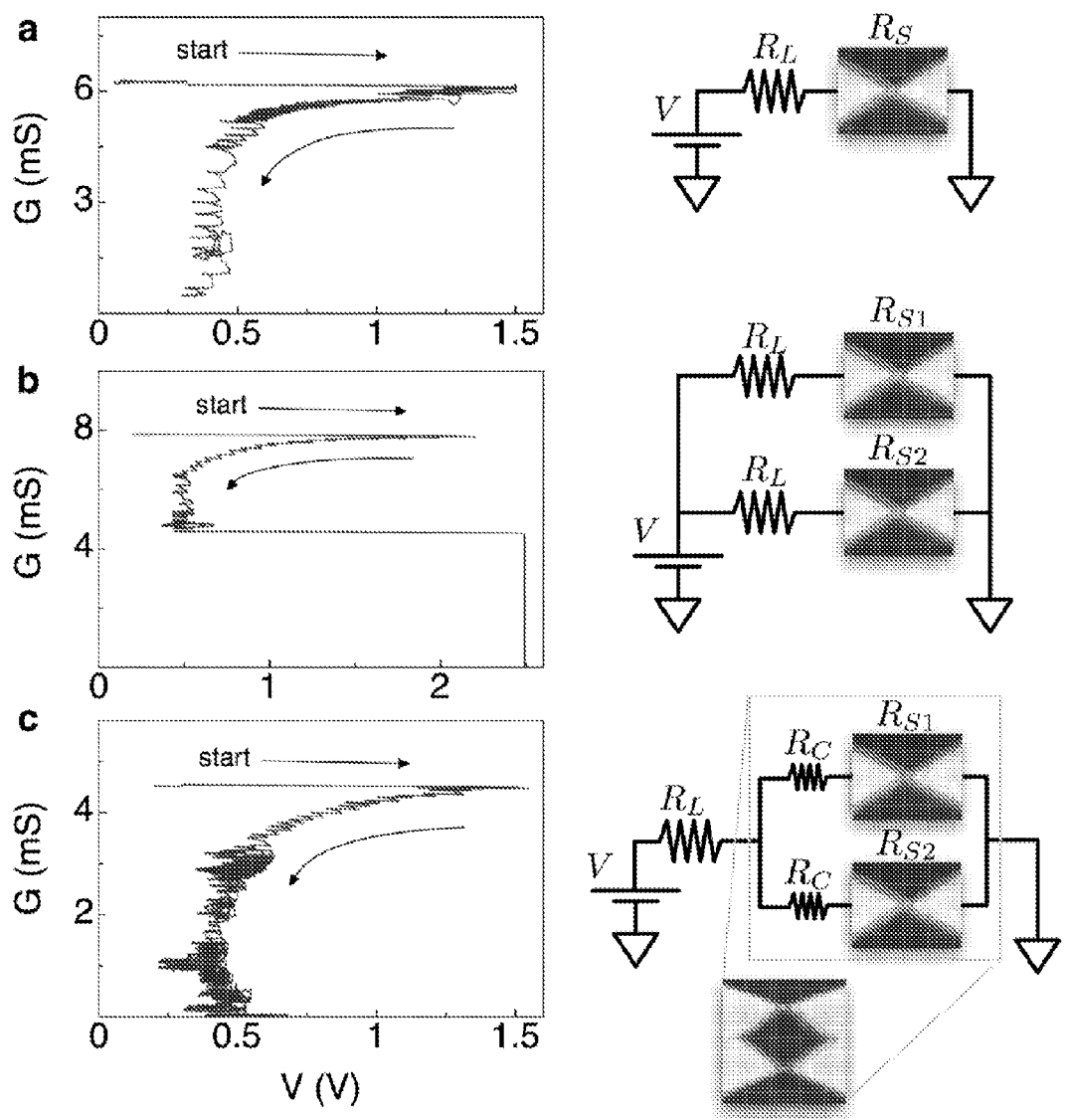
FIG. 1a illustrates a G-V plot of FCE of a single junction, showing smooth controllable decrease in G.
FIG. 1b illustrates two junctions connected by the leads unable to electromigrate together and the thermal runaway occurring when the second junction breaks discontinuously.
FIG. 1c illustrates two junctions connected in parallel by low a resistance Rc and electromigrating in unison in a parallel process.

As used herein, electromigration means the transport of material caused by the gradual movement of the ions in a conductor due to the momentum transfer between conducting electrons and diffusing metal atoms As used herein, junction and constriction are used essentially interchangeably, and means where two or more sections of one or more materials come together at a narrowed location and are in electrical connection.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention that are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

The present invention first provides methods for fabricating a plurality of nanogaps. These methods include controllably applying a voltage across a plurality of constrictions residing in a conductive material comprising a plurality of ions, wherein the constrictions are placed in electrical communication with one another by a conductive material. The electrical resistance between neighboring constrictions is suitably less than the electrical resistance across a constriction.

The controllably applied voltage suitably gives rise to heating within the constrictions, and the heating within the constrictions gives rise to increased electron mobility and migration of ions of the conductive material residing at the constrictions so as to form nanogaps having at least two opposing faces, wherein the mean distance between the opposing faces of the nanogaps being less than about 5 nm, or even less than about 4 nm, or even less than about 3 nm, or even less than about 2 nm, or even less than about 1 nm, or even less than about 0.5 nm. The mean distance of the opposing faces is at least 0.1 nm. Further detail is provided elsewhere herein.

Suitable constrictions include at least one narrowed region. An exemplary, wedge-shaped, constriction is shown in FIG. 1a, where the conductive material is shown to narrow in two directions so as to form a structure with a narrow connection between two broader bodies. A suitably narrowed region includes a characteristic cross-sectional dimension of less than about 30 nm, or even less than about 25 nm, or even less than about 20 nm, or even less than about 15 nm, or even less than about 10 nm. This characteristic cross-sectional dimension is typically greater than about 1 nm. Suitable narrowed regions also include a characteristic width of less than about 100 nm, or less than about 80 nm, or less than about 60 nm, or less than about 40 nm, or less than about 20 nm, or less than about 15 nm. This characteristic width is typically greater than about 5 nm.

Constrictions are suitably wedge-shaped, hourglass-shaped or wire-shaped in structure. Other forms having constrictions will be apparent to those having ordinary skill in the art; as is seen in FIG. 2a, constrictions may be present in a linear configuration of essentially parallel nanogaps.

Figure 2:
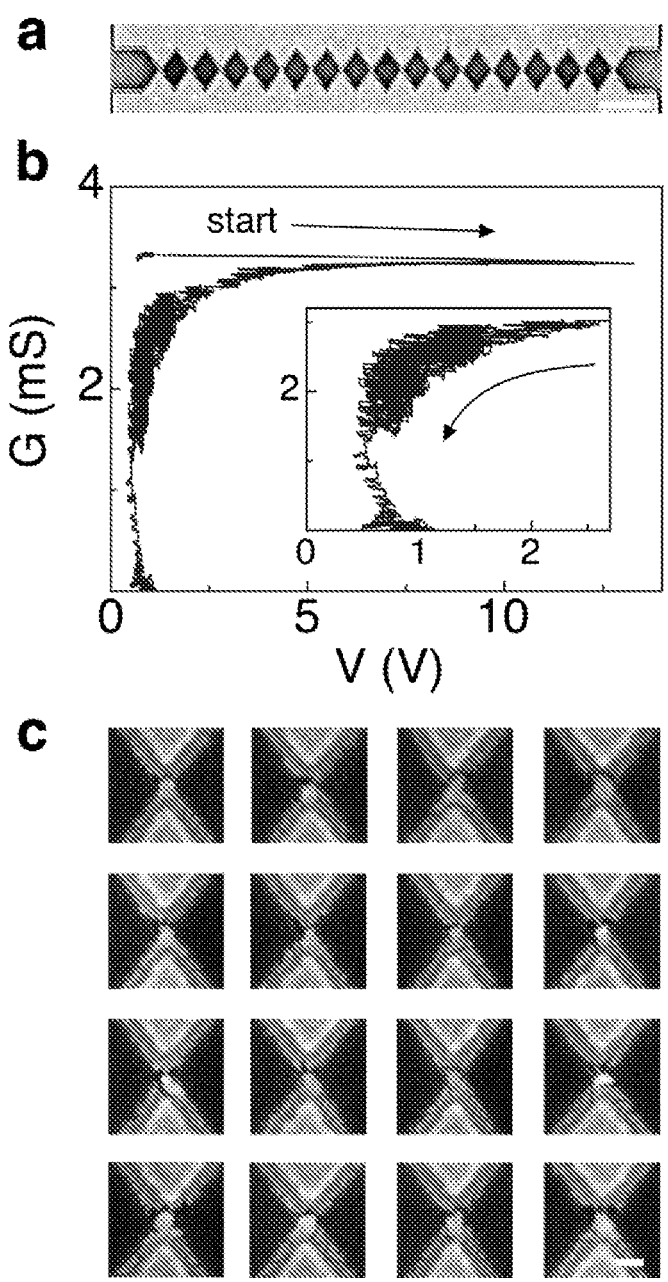
FIG. 2a depicts a scanning electron microscope (SEM) image of an array of 16 junctions made by electron beam lithography and shadow evaporation with a scale bar of 1 micron.
FIG. 2b depicts G-V data from FCE of the 16-junction array.
FIG. 2c depicts SEM images of nanogaps formed by parallel FCE of a 16-junction array clearly showing the gold removed from the thin overlap junctions with a scale bar of 100 nm.

The constrictions are suitably oriented essentially parallel to one another, as shown in FIG. 2a. In certain embodiments, the constrictions are oriented perpendicular to one another or are otherwise arranged according to the user's needs. The constrictions are also, where suitable, arranged in three dimensions so as to create three-dimensional structures having constrictions in several orientations.

Suitable conductive materials include substances nonreactive to air, noble metals, oxide conductors, high-superconducting temperature superconductor, colossal magnetic resistive oxides, inert alloys, graphene, multi-walled nanotubes, or any combination thereof. Suitable noble metals include gold, platinum, palladium, rhodium, ruthenium, iridium, osmium or combinations thereof.

The conductive material is, in some embodiments, a material capable of reacting with air. In such embodiments, the material is suitably sealed against air following fabrication of the nanogaps.

The controllably applied voltage gives rise to heating within the constrictions, which heating in turn gives rise to nanogaps at the constrictions. Without being bound to any particular theory of operation, it is believed that the heating suitably raises the temperature at the heated constrictions to an onset temperature so as to change the mobility of ions at the constriction and then give rise to electromigration of at least a portion of the ions of the conductive material residing at the narrowed regions of the constrictions.

Without again being bound to any particular theory of operation, the electromigration suitably gives rise to displacement of one or more ions of the conductive material from the narrowed regions of the constrictions such that sufficient ions are displaced from the constriction to form nanogaps at the narrowed regions of the constrictions. The displacement of one or more ions of the conductive material from the constrictions suitably causes the destabilization of one or more edges of the constrictions. The nanogaps suitably form simultaneously.

The narrowed regions of the constrictions are suitably separated from one another so as to reduce the effect of the heating of any one constriction on any neighboring constrictions. Such separation distances can be at least about 10 nm, at least about 50 nm, or at least about 100 nm. The separation distances depend on the materials, voltages, and other parameters and will vary according to the needs of the user. The optimal separation distance for a given set of conditions will be apparent to one having ordinary skill in the art.

The electromigration suitably occurs simultaneously within at least two of the constrictions. It is considered especially suitable when the electromigration occurs simultaneously within all of the constrictions.

The nanogaps suitably include at least two opposing faces, which faces are suitably essentially crystalline. It is believed, without commitment to any particular mechanism, that the sequential electromigration of the ions of the conductive material present at the constriction gives rise to the formation of crystalline structures as ions progressively migrate from the constriction.

The mean distance between the opposing faces of the nanogaps fabricated by the present invention is suitably less than about 5 nm. The nanogaps are suitably formed to a degree of precision of about 1 nm, or of about 0.5 nm, or even of about 0.3 nm.

The voltage is suitably controllably applied under vacuum conditions, and is suitably controllably applied at about ambient temperature. The voltage may, however, be applied under other environmental conditions as dictated by the needs of the user.

The controllably applied voltage is suitably in the range of from about 0.2 V to about 2 V per constriction, or in the range of from about 0.5 V to about 1.2 V per constriction, or even in the range of from about 0.8 V to about 1 V per constriction. Other voltage ranges are suitable where material properties so require.

Controllably applying the voltage suitably includes increasing the applied voltage until the conductance value of the conductive material changes. The application of the voltage also includes reducing the voltage until the conductance value of the conductive material reaches a desired value. This value is, in some embodiments, calculated by multiplying the desired conductance of a single nanogap by the number of nanogaps present. Feedback controlled electromigration ("FCE") is considered a suitable method by which to controllably apply the voltage.

The reduction in voltage is suitably performed quickly so as to minimize thermal degradation of the constrictions. In some embodiments, the voltage is decreased about ten times faster than the voltage was increased. As one non-limiting example, the voltage for a given set of constrictions may be increased at about 40 mV/s and then reduced at about 400 mV/s.

For N junctions shorted together, as in FIG. 1c, the stability condition is generalized to $$\frac{\partial P_j}{\partial R_{nj}} < \frac{\partial P_i}{\partial R_{nj}}, \quad (1)$$

where the resistance $R_{nj}$ of junction j is increasing due to electromigration, and $P_i$ is the power dissipated at one of the other (N−1) junctions. Thus, as the resistance $R_{nj}$ at a first constriction j increases as the voltage is controllably applied, the power $P_i$ dissipated at a different constriction increases at a greater rate than the power $P_j$ dissipated at the first constriction.

Further analysis of equation (1) yields $$\frac{2R_L R_\parallel}{R_L + R_\parallel} \cdot \left[ \frac{R_{nj}}{(R_C + R_{nj})^2} - \frac{R_{ni}}{(R_C + R_{ni})^2} \right] + \frac{(R_C - R_{nj})}{(R_C + R_{nj})} < 0, \quad (2)$$

where $$R_\parallel \equiv 1 \bigg/ \sum_{i=1}^{N} (R_C + R_{ni})^{-1}.$$

The junction resistances $R_{ni}$ and $R_{nj}$ are all roughly equal to one another. Thus, the first term in equation (2) is zero to lowest order. The remaining term in equation (2) requires that $R_C < R_{ni} \approx R_{nj}$, which is the resistive condition for stable parallel electromigration. As $R_{nj}$ increases due to electromigration, the left side of equation (2) remains negative which maintains the necessary inequality.

The electrical resistance between neighboring constrictions is suitably less than the electrical resistance across a constriction. This condition in turn permits satisfaction of the stability condition set forth in equation (1).

In some embodiments, at least a portion of the conductive material placing two or more nanogaps in electrical communication is removed, transformed, or both. This is suitably performed so as to reduce electrical communication between two or more of the nanogaps. In some embodiments, it is performed so as to physically separate two or more nanogaps. Such separate nanogaps may then be individually electrically addressed. In other embodiments, it may be preferable to leave some—but not all—nanogaps in electrical connection with one another.

Figure 6:
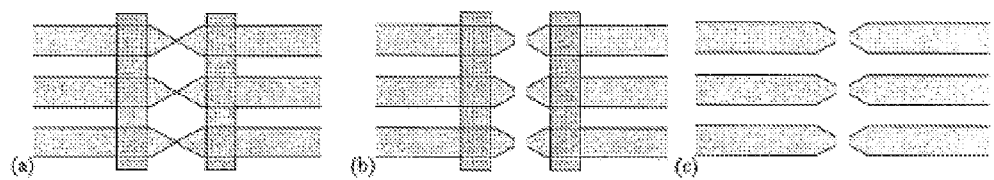
FIG. 6 depicts a scheme for fabricating separate nanogaps using sacrificial material.

A non-limiting representation of this removal process is shown in FIG. 6, which depicts a scheme for fabricating separate nanogaps using sacrificial material. FIG. 6a shows constrictions formed from a first material and connected by a second material. FIG. 6b shows the nanogaps formed by electromigration within the constrictions, and, lastly, FIG. 6c shows the separated nanogaps following removal of the second material. As is seen from the figure, nanogaps can thus be fabricated and then individually separated for further processing or integration into a larger device.

Removal of the conductive material is suitably accomplished by chemical etching, ablating, or other methods known to those having ordinary skill in the art. The transformation of the conductive material is suitably accomplished by selective oxidation, or by other methods known to those having ordinary skill in the art.

The plurality of nanogaps fabricated according to the present method is also within the scope of the invention.

Also disclosed are devices. The disclosed devices include a plurality of nanogaps formed in a first conductive material, the nanogaps comprising opposing electrodes, the opposing electrodes being separated by less than about 5 nm, or any of the nanogap dimensions disclosed herein, the opposing electrodes comprising faces, and the faces of the opposing electrodes being essentially crystalline.

Material suitable for use as the first conductive material are described elsewhere herein, and include substances nonreactive to air, noble metals, oxide conductors, high-Tc superconductors, a colossal magnetic resistive oxide, inert alloys, graphene, multi-walled nanotubes, or any combination thereof. Suitable noble metals are described elsewhere herein.

The separation distance between opposing electrodes of any nanogap suitably varies by less than about 0.3 nm from the mean opposing electrode separation of the plurality of nanogaps. In other embodiments, the separation distance between opposing electrodes of any nanogap varies by less than about the characteristic cross-sectional dimension of a single atom of the conductive material from the mean opposing electrode separation of the plurality of nanogaps.

In the devices, the nanogap electrodes may suitably have the same, or different, conductances. The electrodes may be composed of electrically conductive metals, such as copper, silver, or gold, or may be a semiconducting material, such as silicon, gallium arsenide, and the like.

In some embodiments, a second conducting material places two or more nanogaps in electrical communication with one another, as depicted in FIG. 6. The second conducting material suitably the same as the first conducting material, but, in some embodiments, the second conducting material is different than the first conducting material. The second conducting material is suitably capable of being evaporated, dissolved, or melted. Suitable second conducting materials include chromium, aluminum, or any combination thereof.

In some embodiments, the second conducting material is chosen such that it is capable of being removed, transformed, or both, so as to reduce electrical communication between two or more nanogaps. Second conducting materials capable of being selectively removed, selectively transformed, or both, without affecting the first conducting material are considered especially suitable.

Suitable devices also include one or more molecules residing within one or more nanogaps. In some embodiment, such molecules provide additional functionality to the device. As non-limiting examples, the molecules are capable of detecting the presence of other complementary molecules or of altering the electrical characteristics of the device based on interactions with other molecules.

Amines are considered suitable molecules, and include 1,4-diaminobenzene, 2,7-diaminofluorene, 4,4 0-diaminobiphenyl, 1,3-propanediamine, N,N'-dimethylpropane-1,3-diamine, and N,N,N',N'-tetramethylpropane-1,3-diamine, 1,4-butanediamine, or any combination thereof. Amines can suitably include an aromatic ring.

In certain embodiments, one or more of the nanogaps is individually electrically addressable. This is depicted in FIG. 6c, where three individually-addressable nanogaps are shown.

As described elsewhere herein, the nanogaps may oriented essentially parallel to one another, as shown in FIG. 2a. In other embodiments, the constrictions are oriented perpendicular to one another or are otherwise arranged according to the user's needs. The nanogaps are also, where suitable, arranged in three dimensions so as to create three-dimensional structures that present nanogaps in several orientations.

The present invention also includes sensors, displays, electrical circuits, detectors, imaging devices, nanocrystal devices, tuned plasmonic wave guides, magnetic spin valves, or electrical circuits of colloidal aggregate devices that include the nanogaps disclosed herein. The disclosed nanogaps are also suitable for incorporation into metamaterials.

Examples and Illustrative Embodiments

The following examples and illustrative embodiments are representative only and do not necessarily limit the scope of the present invention.

Sample Fabrication

FCE samples, consisting of a thin, narrow gold junction connected to thick gold leads, were fabricated using electron beam lithography and angle evaporation. Electron beam lithography was used to pattern two electrodes whose ends were separated by 150 nm. For samples comprising an array, junctions were spaced by about 600 nm. A bi-layer resist system was selected to guarantee a large undercut region, such that angle evaporation could be used to form the thin, narrow junction underneath a suspended resist bridge. The lower resist layer comprised 500 nm of a copolymer (MicroChem Corp, EL9), while the upper layer comprised 100 nm of polymethylmethacrylate (PMMA) (MicroChem, 950PMMAC2).

After electron beam exposure, the pattern was developed in a 3:1 solution of isopropanol and methyl isobutyl ketone for 45 seconds. Thin film deposition was performed in a thermal evaporator (base pressure below $10^{-6}$ Torr) equipped with a rotating sample stage. Metallization consisted of about 3 nm Cr deposited normal to the substrate, about 12 nm Au deposited with the sample rotated by about $\pm 11°$ to form the thin metal junction, and finally, about 30 nm gold deposited normal to the substrate.

Experimental Results and Additional Discussion

FIG. 1a shows the time evolution of the conductance-voltage (G-V) characteristic of a single thin gold junction during FCE and the resistor model used to analyze these data. The resistor model, see Strachan, D. R.; et al., *Appl. Phys. Lett.* 2005, 86, 043109, consisted of a lead resistance, $R_L$, in series with a variable junction resistance, $R_n$. During FCE of a single junction, a rapid increase in $R_n$ due to electromigration occurs upon reaching a critical level of power dissipation and a critical temperature at the junction. Strachan, et al., *Appl. Phys. Lett.*, 2005, 86, 043109; Esen, G.; et al., *Appl. Phys. Lett.* 2005, 87, 263101; Trouwborst, M. L.; et al., *J. Appl. Phys.*, 2006, 99, 114316. This behavior is characteristic of a junction in the bulk-neck regime where its diameter exceeds one nanometer. Strachan, D. R.; et al., *Appl. Phys. Lett.* 2005, 86, 043109.

Single Constriction

In response to an increase in overall resistance, the active feedback loop adjusted V, thereby tracing out the single junction electromigration G-V curve illustrated in FIG. 1a. The smooth decrease in G over as many as 11 orders of magnitude reflected the controlled electromigration process, where thermal runaway and stochastic breaking of the nanogap are avoided.

Connected Junctions Not in Parallel

If this approach is scaled up by simply connecting two leads together (FIG. 1b) FCE consistently failed to make uniform nanogaps in parallel. Instead, gaps formed sequentially, as in the G-V curve of FIG. 1b. (Sequential gap formation was observed in 4 out of 4 trials.) It is believed, without being bound to any one theory, that this behavior was due to the inherent variability of nanolithography. That is, one of the thin junctions (e.g., junction 1, having resistance $R_{n1}$) would begin to experience electromigration at a smaller applied voltage than the other junction (the junction having resistance $R_{n2}$). As a result, junction 1 would undergo controlled electromigration until one nanogap is formed, and the resistance of the parallel combination of the two junctions then becomes pinned at $R_{n2}$. At this point the voltage increases sharply, and the second junction fails in an abrupt, uncontrollable break.

Figure 4:
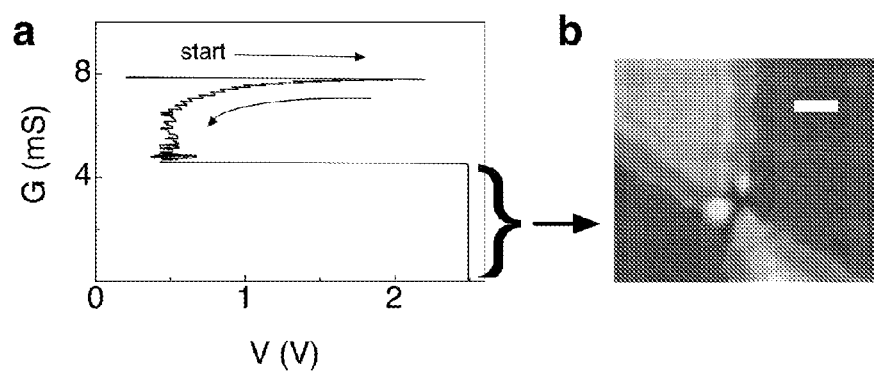
FIG. 4a illustrates G-V data for a constriction undergoing melting due to sequential electromigration.
FIG. 4b depicts a SEM image of the second gap formed showing a spherical build-up of gold (scale bar is 100 nm)

Due to the sequential nature of the process, at some point the junction resistances differed by orders of magnitude (junction 1 being in the tunnel regime with $R_{S1} \gg h/2e^2 \sim 12$ k$\Omega$, while $R_{n2}$ remains at its initial value near 4$\Omega$), and simultaneous control over both junctions was impossible. An additional consideration is that the first nanogap was subjected to a large voltage after it is formed, which large voltage can alter the gap. Further, undesirable melting, indicated by a spherical build up of gold at the gap edge, was discernible by scanning electron microscopy (SEM) in some of the sequentially formed junctions, as seen in FIG. 4.

Parallel FCE can be obtained by considering the variation in the power dissipated at each junction upon a change in the resistance of the weaker junction, $R_{n1}$. As $R_{n1}$ increases due to electromigration, the power $P_2$ dissipated in $R_{n2}$ must increase at a greater rate than $P_1$ such that $$\frac{\partial P_1}{\partial R_{n1}} < \frac{\partial P_2}{\partial R_{n1}}. \qquad (3)$$

When equation (3) is fulfilled for a suitable system, the electromigration naturally balances between the two junctions and they can evolve together. Thus, equation (3) represents an essential stability criterion for parallel electromigration. Returning to the simple case of FIG. 1b, the power dissipated by $R_{n2}$ is unaffected by changes in $R_{n1}$ when the lead resistance $R_L$ is much larger than both $R_{n1}$ and $R_{n2}$, so that the stability condition is clearly not satisfied.

Junctions Connected in Parallel

A circuit design that resulted in an effectively parallel FCE process is shown in FIG. 1c. In this case, the junctions shared a common series lead resistance $R_L$ and were connected together by low resistances $R_C$. As discussed elsewhere herein, when $R_C < R_{n1}, R_{n2}$ the stability condition (equation (3)) is satisfied and the nanogaps evolve together. As the resistance of the weakest junction increase, current is diverted to the other junction and increases its power dissipation and rate of electromigration. This is illustrated by the G-V curve, in FIG. 1c, of a pair of shorted nanogaps being electromigrated together. The smooth FCE process was qualitatively indistinguishable from that of a single junction with no evidence of thermal runaway. Parallel FCE of pairs of shorted nanogaps resulted in smooth G-V curves in 3 out of 3 trials.

The described process was extended to the parallel formation of larger arrays of nanogaps, as demonstrated with the 16-junction array pictured in FIG. 2a. The G-V diagram measured during FCE of the 16-junction array is shown in FIG. 2b.

The electromigration process of the array was remarkably similar to that of the single junction (FIG. 1a). The time required for the FCE process was essentially the same as the time required for the single junction case, while the measured currents and voltages were scaled-up by the number of junctions as expected. FIG. 1c shows images of the resulting nanogaps, which are in good agreement with other reports of SEM images of individual nanogaps formed by electromigration. SEM images of the present invention did not have sufficient resolution to determine the final distribution of gap sizes. For this reason, it is believed that the single smooth FCE process of the array is currently the best indication that the nanogaps evolve in parallel. The future development of arrays compatible with transmission electron microscopy and satisfying the stability condition (equation (3)) will enable the direct determination of the nanogap distribution.

Further evidence that this circuit design leads to parallel FCE of the junctions was seen from an analysis of the bulk-neck regime. The bulk neck regime is characterized by a constant critical power, P*, dissipated at the junction which triggers electromigration.

Figure 3:
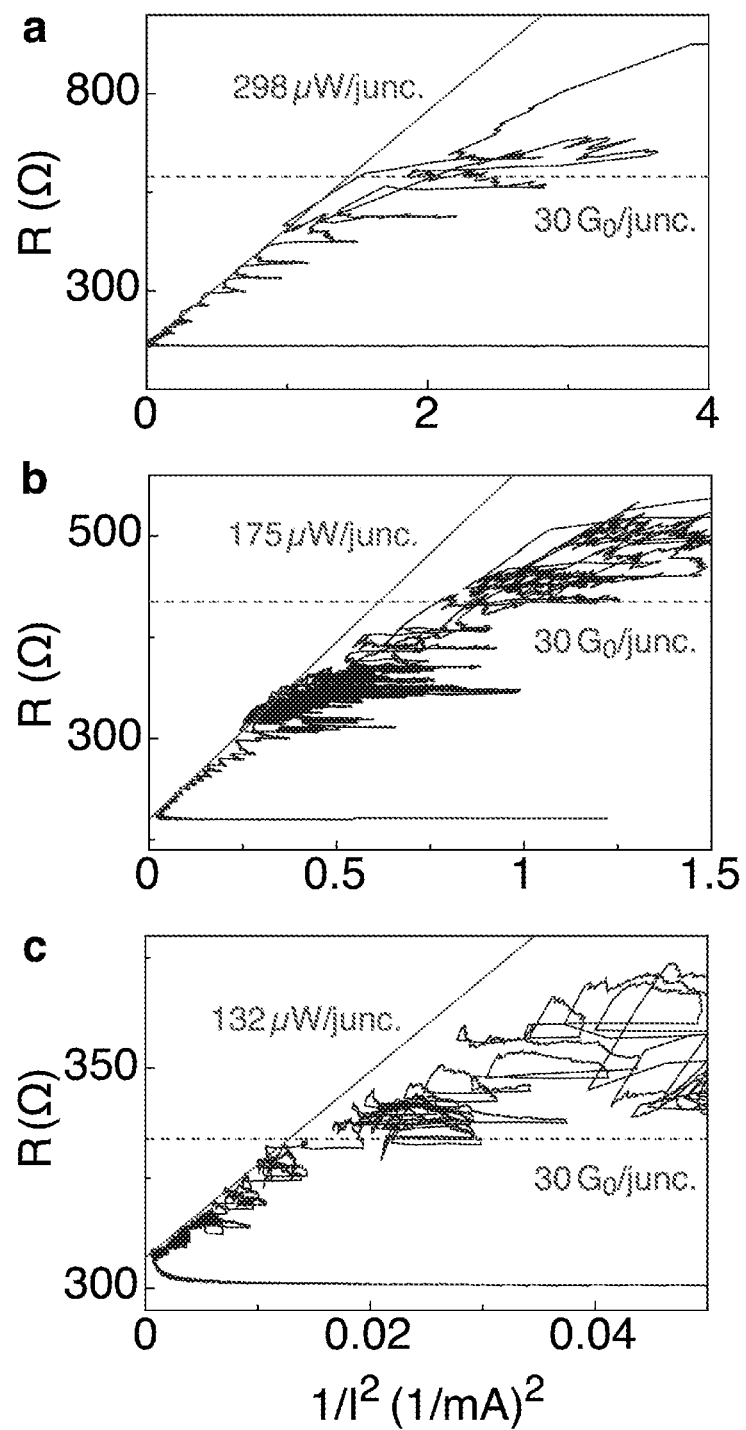
FIG. 3 illustrates FCE data from gold junctions undergoing parallel electromigration with a linear fit to a critical break power model for (FIG. 3a) a single junction, (FIG. 3b) two junctions connected by low inter-junction resistance paths, and (FIG. 3c) for a 16-junction array.

Without being bound to any one theory of operation, it is believed that this analysis implies $R=R_L+P^*/I^2$, such that a plot of R versus $1/I^2$ should be linear with a slope equal to the power dissipation. As shown in FIG. 3a, this relationship held when the junction resistance was relatively low, with observable deviations from bulk behavior when the conductance of the junction became less than $30G_0$. A similar deviation occurred for the case of two junctions in parallel (FIG. 3b) and for 16 junctions (FIG. 3c) when the array conductance was less than $30G_0$ per junction. This was indicative of a characteristic change in the nanogap evolution when its conductance fell below $\sim 30G_0$ corresponding to a gold metallic contact with diameter of about 1.5 nm or approximately six atoms (assuming each atom contributed conductance $G_0$, and that the atomic radius of gold is about 0.14 nm). The range of critical powers found from the fits in FIG. 3 was within the typical variability of device parameters. Not being bound to any single theory, it is believed that the decrease in critical power per junction with increasing N indicated the effect of heating from other nearby junctions.

Figure 5:
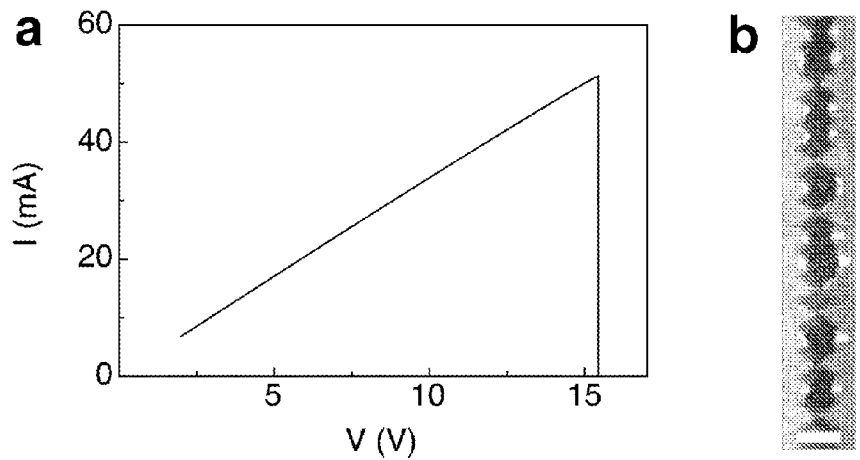
FIG. 5a depicts single voltage ramp electromigration of 16 Au junction array as an applied voltage is ramped across the array at 58 mV/sec until failure occurs, and (FIG. 5b) a SEM image after failure (scale bar is 1 micron)

Without again being bound to any single theory of operation, it is believed that the arrangement having electrical shorts (FIG. 1c) may not be compatible with the single ramp technique. Because of the resistance $R_L$, the applied voltage needed to initiate electromigration increases with the number of junctions. Thus, as the nanogaps open and their resistances increase during the single ramp procedure, it is believed that the applied voltage will fall almost completely across the open nanogaps, which may lead to damage and a result in a majority of gaps having spacings in excess of 0.5 microns (FIG. 5).

Sequential Gap Formation and Melting

Melting was discerned by scanning electron microscopy (SEM) of certain gaps formed through the sequential electromigration process. The spherical build-up of gold shown in FIG. 4 evidenced such melting.

Single-Ramp Electromigration of 16-Junction Array

As contrasted with FCE, the majority of junctions in an array of electrically shorted gold junctions with low inter-junction resistances were destroyed by single-ramp voltage application process. The resulting gaps exhibited a range of gap sizes, with the majority—9 out of 16—having widths larger than about 0.5 microns (500 nm), as illustrated in FIG. 5.

Additional Embodiments and Applications

1. Tuned Plasmonic Wave Guides Using Nanogap Arrays

Controlling the flow and interaction of light on a size-scale smaller than its wavelength may be significant for nano-photovoltaic applications. This is due to the possibilities of guiding the flow of its energy, and strongly coupling light to devices on the nanometer scale, with the possible implications for directing light energy towards nano-scale photovoltaic and other light-activated devices.

Figure 7:
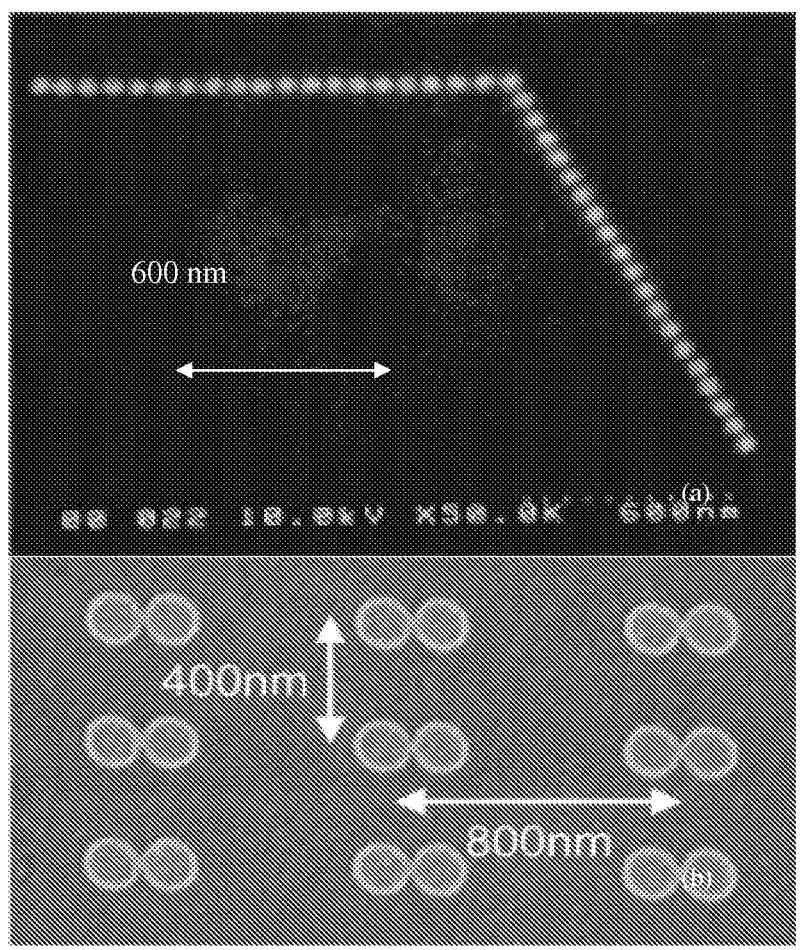
FIG. 7a depicts a waveguide array of metallic dots reproduced from Maier, S. A., et al., Nature Materials 2, 229 (2003)
FIG. 7b depicts a dimer array that enables hybridization and field enhancement at the colloidal junctions reproduced from Lalayan, A. A., et al., J. Appl. Phys. 91, 2965 (2002)

Examples of such approaches are nano-arrays (FIG. 7a) and dimers (FIG. 10) which funnel and focus the energy derived from light. Specifically, dimers (as in FIG. 10) have received widespread interest due to the extreme field enhancement that occurs at the location of closest proximity in the nanogap region between the two colloids. The techniques of Hongxing Xu, Javier Aizpurua, Mikael Kall et al., Phys. Rev. E 62, 4318 (2000) can be applied hererin.

Other work has shown that plasmonic resonances can be finely tuned through hybridization of the individual colloid resonances through the fine tuning of the nanogap distance between the colloids. The techniques of Tolga Atay, Jung-Hoon Song, and Arto V. Nurmikko, Nano Lett. 4, 1627 (2004); Matthias Danckwerts and Lukas Novotny, Phys. Rev. Lett. 98, 026104 (2007) can be applied herein. Arrays of such nano-dimers could be used to funnel light energy of specific frequencies in various directions within a single chip and "superfocusing" it down to individual photovoltaics or devices. The techniques of A. A. Lalayan, K. S. Bagdasaryan, P. G. Petrosyan et al., J. Appl. Phys. 91, 2965 (2002) can be applied hererin. This could enable a more efficient use of the entire radiation spectrum since energy could be directed only towards the nano-scale devices on the chip most suitable for that frequency. Though advances have been made, the challenge of fine-tuning the atomic scale critical dimensions of the colloidal gap sizes to achieve precise control over the necessary near-field coupling between adjacent colloids and dimmers remains. The techniques of Tolga Atay, Jung-Hoon Song, and Arto V. Nurmikko, Nano Lett. 4, 1627 (2004); Stefan A. Maier, Mark L. Brongersma, Pieter G. Kik et al., Adv. Mater. 13, 1501 (2001) can be applied herein.

Figure 8:
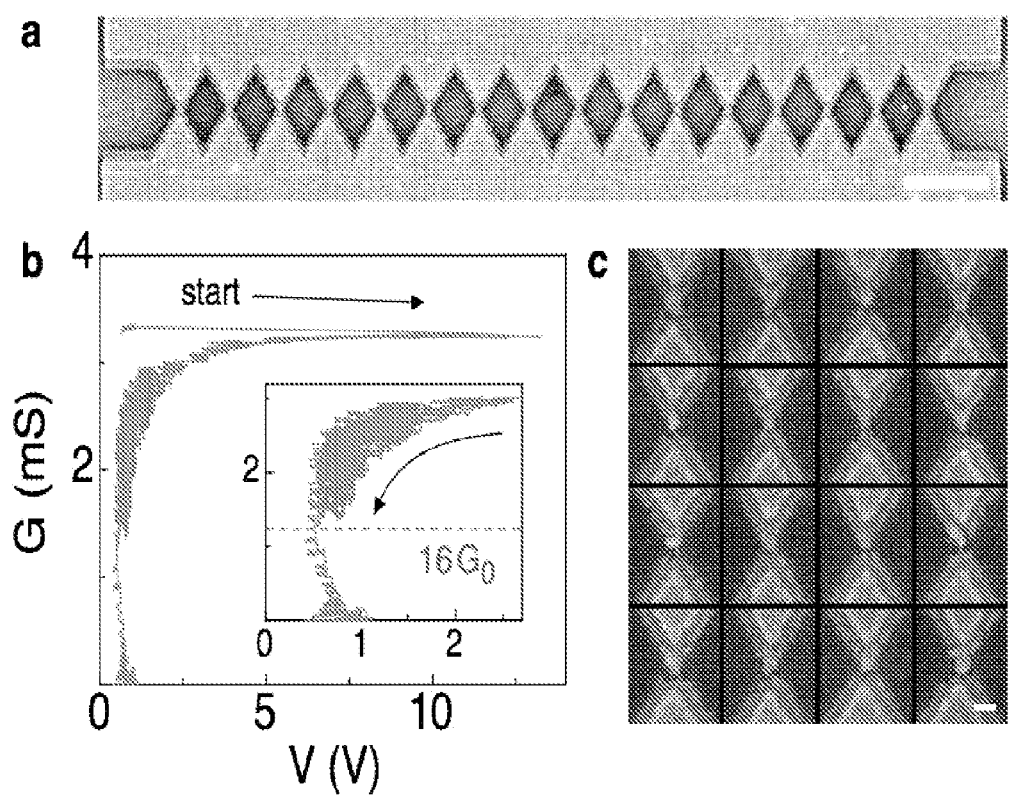
FIG. 8a depicts an array of gold weak links with a 1 micron scale bar.
FIG. 8b depicts the G-V behavior of the array.
FIG. 8c illustrates the array of finally-formed (100 nm scale bar)

The disclosed nanogap arrays could be used as plasmon wave guides and as "superfocusing" junctions. One such array of 16 junctions is shown in FIG. 8, where the nanogaps were formed simultaneously in a controlled electromigration procedure. The major benefit of this array is that it contains nano-scale junctions that can be tuned in size, thus in turn allowing fine-tuning of the plasmon resonances. The techniques of Hiroharu Tamaru, Hitoshi Kuwata, Hideki T. Miyazaki et al., Appl. Phys. Lett. 80, 1826 (2002) can be applied herein.

Figure 9:
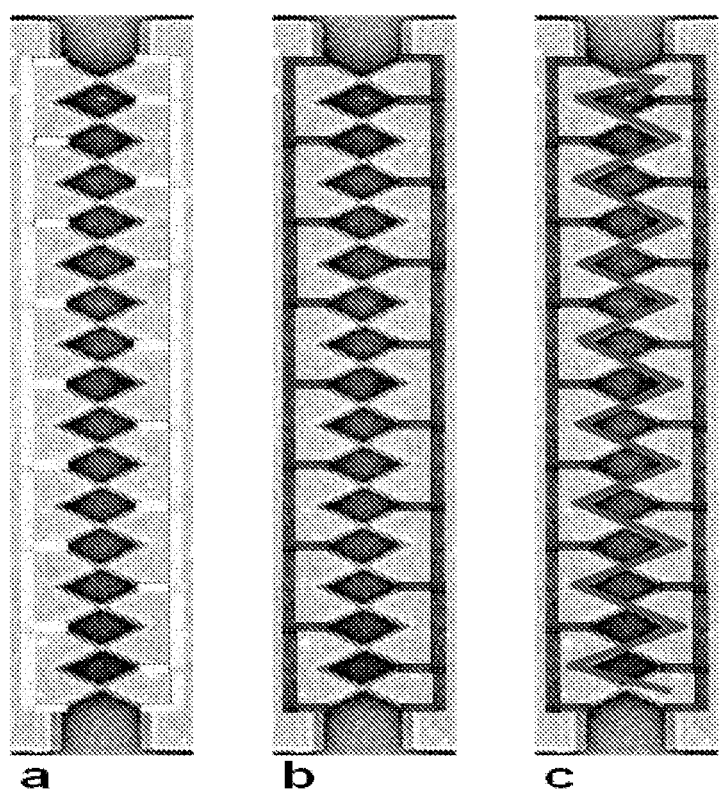
FIG. 9a depicts an array of narrowed constrictions overlaid with schematic representation of sacrificial shorts (lightened regions)
FIG. 9b depicts the array after electromigration followed by selective etching that leave gold islands separated by nanogaps.
FIG. 9c depicts the array propagating light of a specific frequency depending on the nanogaps' size.
Figure 10:
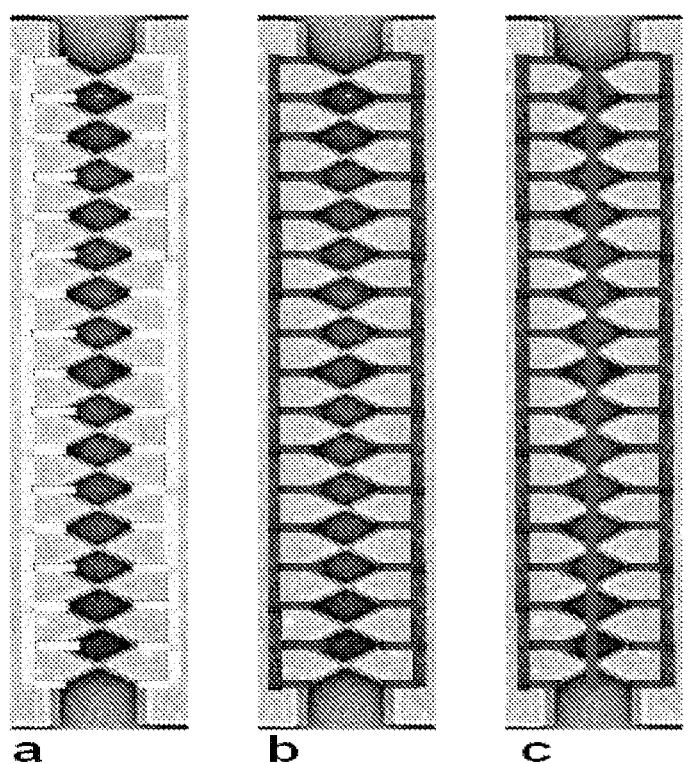
FIG. 10 depicts an alternative geometry and mode of light propagation for the array of FIG. 9, showing the generality of the technique.

To use the array as a wave guide, portions of the bulk leads in FIG. 9a (which join up to the nano-junctions) could be selectively etched away so as to force the plasmons to either zigzag up and down along the array (FIG. 9) or to travel between adjacent nanogaps (FIG. 10). Used in this way, the array acts as a chain of metallic dots with a highly tunable inter-dot near-field coupling.

Figure 11:
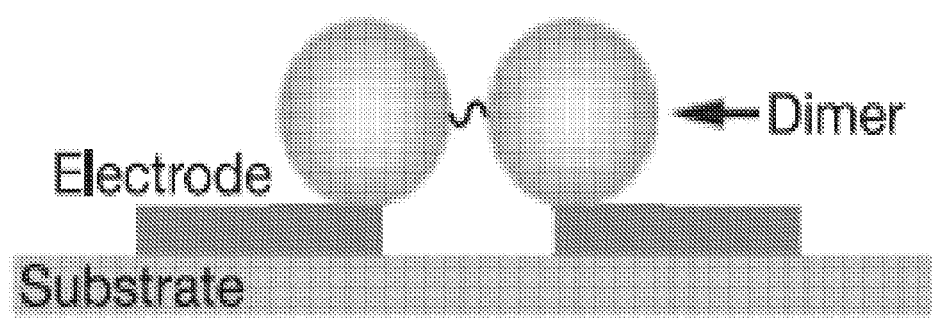
FIG. 11 depicts a dimer bridged with a molecule, reproduced from T. Dadosh, et al., *Nature* 436, 677 (2005)

The array of nanogaps could also be used to electrostatically trap very small dimers that are formed in solution with an intervening molecule. This is similar to a recent technique developed to fabricate single molecule transistors, T. Dadosh, Y. Gordin, R. Krahne et al., Nature 436, 677 (2005), as illustrated in FIG. 11, which can be applied herein.

Figure 12:
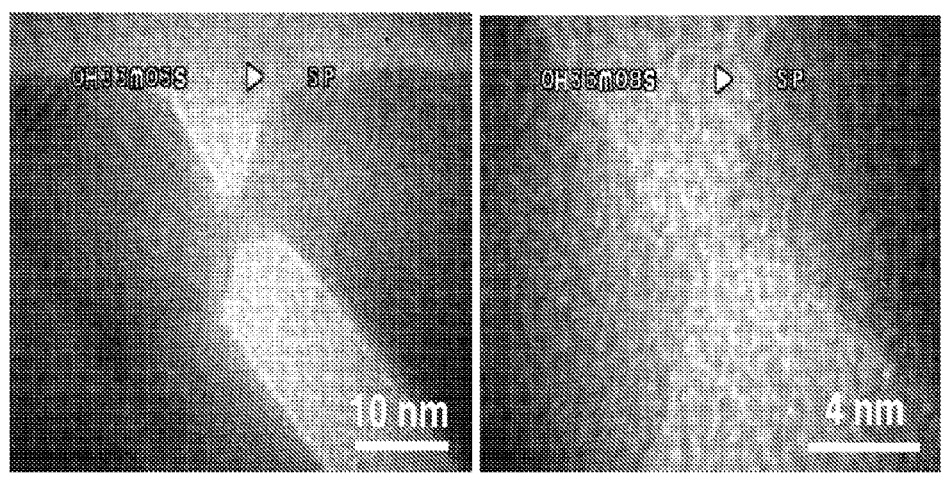
FIG. 12 illustrates TEM images of controlled electromigrated nanogaps showing the highly ordered crystal facets.

After the dimmer array is constructed through electrostatic trapping, the array can be used as a wave guide with a precisely tuned resonance frequency determined by the molecular spacer. The work with colloidal dimers can also be extended to larger, more complex structures of colloids through aggregation in solution. In addition, arrays of small dimer structures could find utility in improving surface-enhanced Raman spectroscopy of single molecules, and in applications towards meta-materials. The techniques of A. N. Grigorenko, A. K. Geim, H. F. Gleeson et al., Nature 438, 335 (2005) can be applied herein. Also, the well-formed facetted edges, as shown in FIG. 12, can be suited for "superfocusing" of the plasmonic modes at nano-scale devices or photovoltaics. In this regard, the techniques of A. A. Lalayan, K. S. Bagdasaryan, P. G. Petrosyan et al., J. Appl. Phys. 91, 2965 (2002) can be applied herein.

2. Colloidal Aggregate Transistors

Single molecule electronics may greatly increase transistor speed, decrease transistor size, and act as highly specific chemical sensors. Due to their small size, slight structural variations of molecular devices can cause drastic changes in behavior by affecting tunnel barriers, capacitive charging energies, stability, and ability to gate. Thus, making reproducible molecular devices is a significant challenge and such devices are susceptible to many artifacts. Control over the atomic-scale structure of molecular devices is thus of importance.

One approach is to bridge a molecule between two colloidal gold spheres in solution to form a dimer structure (FIG. 11) and then to bridge this between 50 nm spaced electrodes, so that the colloidal spheres form extensions of the leads. A benefit of this method is that the dimer is formed in solution so that it naturally accommodates the molecule's size and shape. However, because the 30 nm colloidal spheres screen the applied electric fields from the gate, forming a transistor with this technique poses significant challenges.

A solution to this is to use smaller 3 nm diameter colloidal spheres and to combine this with electromigrated nanogap electrodes of the present invention. The electrodes have a reproducible separation less than 5 nm and could easily be bridged by dimers formed by 3 nm colloids. The smaller spheres will significantly reduce the screening of the molecule so that gating and, consequently, formation of a transistor should be possible. In addition, the smaller masses of the colloids should result in stiffer dimers with much less variability of their structure.

3. Nano Magnetoresistive Spin Valves and their Atomic Scale Structure

Large magnetoresistive effects in nanometer-scale magnetic leads have been reported and could be of considerable technological importance as quantum spin valves and in molecular devices made from magnetic leads. The techniques of A. N. Pasupathy, R. C. Bialczak, J. Martinek et al., Science 306, 86 (2004) can be applied herein. The controlled electromigration techniques described herein can be used to make atomic-scale magnetic devices anchored to a substrate. These techniques significantly reduces spurious magnetostrictive effects where device geometry is altered due to the interaction with applied fields. The results indicate that the atomic-scale structure of these junctions can significantly alter the magnetoresistance of the devices by altering the nanometer-scale magnetic domain structure or by altering the current injection angles near to the junction.

Highly crystalline nanogaps of the present invention, formed using the controlled electromigration-on-membrane, could be used in magnetic spin valves. The clean crystal planes that are formed through the controlled electromigration process, as is evident in FIG. 12, provide highly ordered and reproducible surfaces to control the magnetic domain orientation in the leads.

Furthermore, the surface migration mechanism that occurs in the evolution of metallic nano-junctions, also permits precise nano-structure formation of colossal magnetoresistive (CMR) oxides—even though they are brittle materials. This enables spin transport studies to the nano-scale of these important materials.

Application to Brittle Materials

Here we provide a novel technique to form these junctions in brittle materials which are not easily formed into these atomic-scale structures by pulling. The technique relies on fabricating a narrow constriction within the brittle material and then using computer controlled electromigration (CCE) to gently form a crystalline nano-scale junction. A major advantage of our technique is that these junctions should be highly crystalline due to an unzipping process which cleans up the crystal surfaces.

Controlled Electromigration Produces Crystalline Nano-Junctions

Figure 13:
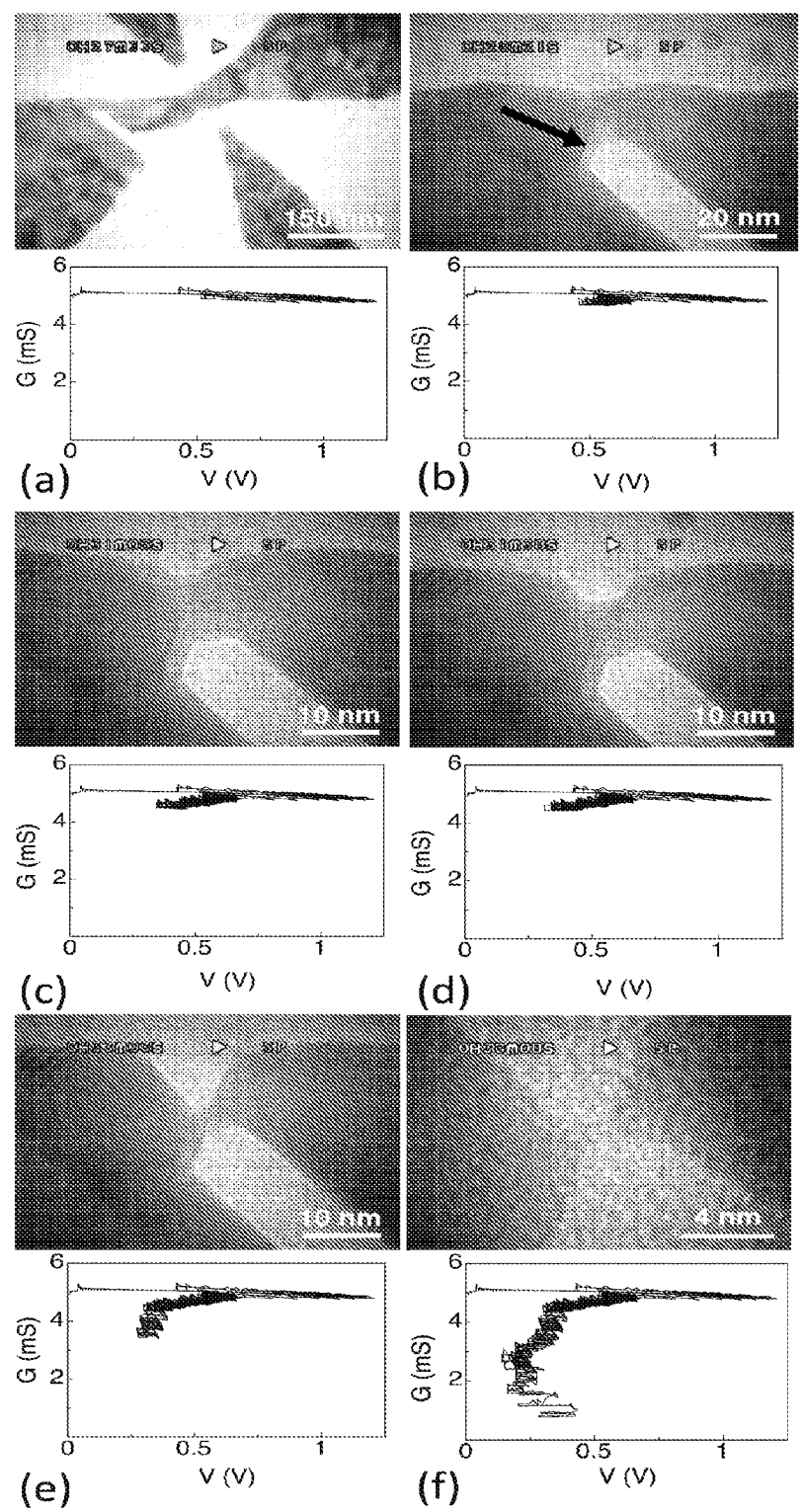
FIG. 13 (a) shows an image of a forming nanogap (where Au is dark) part way through a controlled electromigration procedure with the corresponding conductance-voltage curve; (b) shows higher resolution image of real-time controlled electromigration showing crystal faceting and thinning; the arrow points out a step edge; (c) shows a hexagon placed in the void—indicative of electromigration along the high mobility <110> crystal directions of {111} oriented Au; (d) shows the start of electromigration along the top edge, where crystal faceting now becomes there and progresses to image in (e); (f) shows the lead pinched down to about 1 nm in size, corresponding to approximately 10 atomic channels of conduction.
Figure 14:
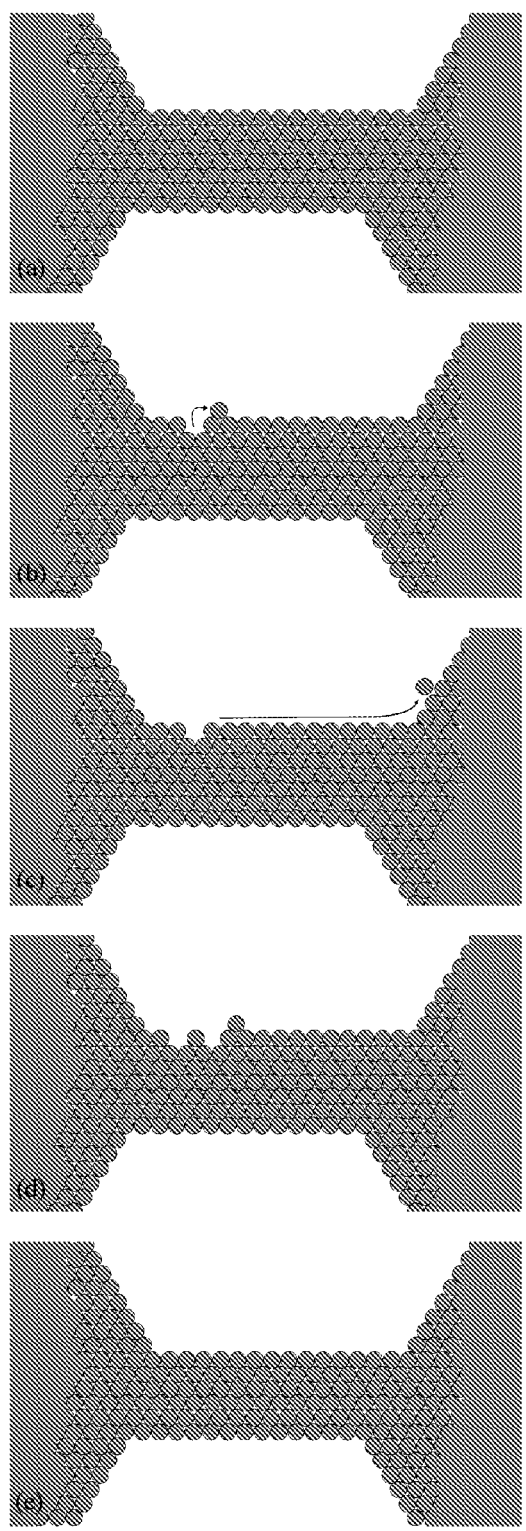
FIG. 14 shows an unzipping model of controlled electromigration evolution of a nanowire; starting with the initial wire in (a), the edge ions are the easiest to thermally excite as in (b); these excitations are easy to electromigrate away in (c) since they have a much higher mobility; this leaves an edge vacancy that allows for further ease of electromigration and excitation to the edge since the number of nearest neighbors is reduced for nearby ions in (d); this quickly destabilizes the edge and allows for easy electromigration of the layer in (e)

Hereinabove is described the dynamics of the formation of nano-scale junctions using real-time imaging of CCE. The results indicate an evolution based on a simple unzipping model. FIG. 13 shows the evolution of a gold nano-junction as it is electromigrated. The important characteristic to notice amongst the six images is that as the nano-electrode is electromigrated it is pinched in along crystal planes. The evolution of the crystal planes is well described by a simple unzipping model we have recently proposed. This model is illustrated in FIG. 14. At a critical temperature, the edge atoms are excited as shown in FIG. 14b. These excitations are easily pushed to the side by the applied current, which leaves a vacancy that is unstable towards further excitation and electromigration. Thus, a layer-by-layer removal of the edge of the lead occurs that results in a crystalline nanometer-scale junction.

Electromigrating Brittle Materials

One difference between CCE and pulling a nano-scale junction is that the center of mass of each lead on either side of the junction is kept fixed with respect to the other in the former case. In contrast, when a junction is pulled the center of mass of each lead is pulled with respect to the other. This requires major readjustments of the crystal structure near the vicinity of the junction which is not achievable for brittle materials. In the case of CCE, only the least bound edge ions are excited and moved, thus avoiding the need for any major crystal rearrangements. As a result, the CCE technique is applicable to forming nano-scale junctions in a much broader array of materials—including materials that are brittle.

Applying the CCE technique to brittle materials uses a modified procedure. Consider the device represented by the schematic of FIG. 15a where a brittle material is connected by two metallic leads. A schematic of such a nanometer-scale structure conveys the fact that the lines are not nearly straight on (roughly) the sub 30 nm size-scale, as depicted in FIG. 15b. The problem is that by attempting to electromigrate the structure of FIG. 15b, instead of forming a narrow junction within the brittle material, the junction appears near the contact between the metallic contact and the brittle material. Without being bound by any particular theory of operation, the reason for this is partly due to the fact that the ion and electron mobility of the metallic lead is typically much larger than those of the brittle material. In addition, the region most susceptible to electromigration is the joining region where changes in material properties and temperature gradients are greatest.

To overcome the deleterious electromigration at the metallic contact, a nano-lithographically formed constriction within the brittle material is first fabricated. This will cause the region of greatest temperature and current density to be well within the region of the brittle material and far away from the metallic contact. The constriction that is formed will not have well-ordered crystalline surfaces due to limitations with nano-lithography, as represented in FIG. 15d. However, once there is a constriction that can allow the least bound edge ions to be dislodged according to the model of FIG. 14b, the edges of the constriction will unzip and form crystalline surfaces. By utilizing CCE, this method can be continued until a suitable nano-scale junction is formed with crystal surfaces, despite the fact that the initial constriction was not atomically smooth.

Electromigrating Brittle Materials: Details of Methods to Fabricate Nano-Junctions in Brittle Materials.

Several techniques are provided to form the required narrow constriction in a brittle material that allows CCE to achieve an ordered nano-scale junction.

Thin Film Geometry

Figure 15:
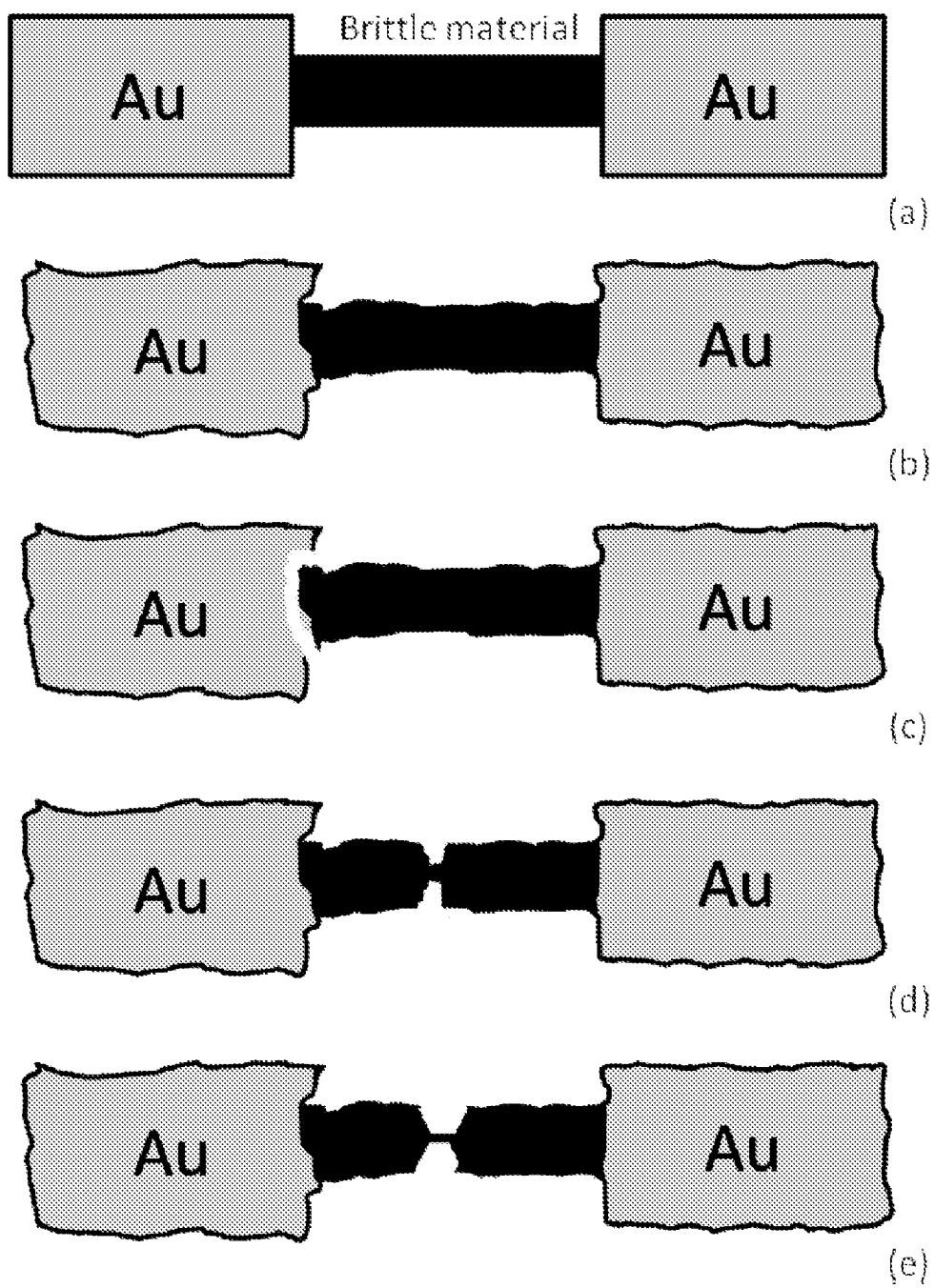
FIG. 15 shows a schematic outlining the fabrication of an ordered nano-scale junction within a brittle material; (a) shows the general schematic; (b) shows a more realistic representation with the leads not precisely determined with nano-lithography; (c) shows the typical deleterious electromigration that occurs at the metallic contact; (d) shows a narrowed constriction that can be used to avoid the electromigration at the metallic contact; (e) represents the resulting crystalline ordered nano-scale junction after CCE is performed.

For thin films of brittle material that may be achieved through several techniques (such as pulsed laser deposited, molecular beam epitaxial (MBE) deposition, or "scotch tape" thinning) the appropriate narrow constriction can be achieved through standard electron-beam nano-lithography. Starting with a sheet of the brittle material, metallic electrodes can be placed at the ends, as depicted in FIG. 15$b$. At this stage electron-beam lithography can be used to cover the entire structure with e-beam resist except for two wedge-shaped regions in the middle of the bridge. These wedge-shaped regions can then be removed by ion-milling, chemical etching, or reactive-ion etching to leave the structure shown in FIG. 15$d$.

Nano-Wire Geometry

Starting with a nano-wire, two metallic leads can be connected to the ends as shown in FIG. 15$a$ by using standard electron-beam lithography. A narrowed constriction in the nano-wire can be obtained by milling with a focused ion beam (FIB). Alternatively, one could also use electron-beam lithography to place resist everywhere except for a thin (~100 nm wide) strip in the middle of the wire. Then ion-milling, chemical etching, or reactive ion etching could then be used to partially remove the nanowire material in the strip region—leaving a narrowed constriction there. The unzipping process has been demonstrated in narrow Au wires. This technique can be further applied to other materials, such as a graphene sheet that has a lithographically defined narrow constriction.

Applications and Uses of Nano-Junctions in Brittle Materials:

As the size-scale of electronics decreases, the utility of nano-scale junctions will increase. Two applications of the electromigrated nano-junctions in brittle materials relate to graphene and high-Tc superconductors—both of which are brittle materials. Below is outlined applications of nano-junctions in several brittle materials.

Graphene:

Single layers of graphene have recently received great interest due to the fact that it is the essential component of carbon nanotubes. The excitement stems from the fact that graphene could be utilized to form devices similar to carbon nanotubes, but without the inherent difficulty in placement and sorting. Nanotube-like devices can be lithographically fabricated directly from a sheet of graphene, so that they can be integrated directly into nano-electronics. Fabricating such devices requires strict control over the atomic scale details of the edge of the graphene sheet. The methods described herein are capable of forming and controlling the edge of a graphene sheet that is formed into a nano-scale junction. In one embodiment of the fabrication technique, the resulting contacts are also made of graphene. Graphene contacts avoids problems associated with Schottky barriers, which can plague devices made of carbon nanotubes. Furthermore, since CCE migrates ions along the high mobility crystal directions, as shown in FIGS. 13 and 14, the processes disclosed herein are capable of producing graphene devices that are highly reproducible since they will be determined by the underlying crystallinity of the graphene. Fabricating devices from graphene represents a major benefit over the random construction of carbon nanotube devices that are currently constructed.

High-Tc Superconductors:

High-Tc superconductors have many potential electronic uses such as Josephson junctions, low-impedance nano-scale interconnects, and bolometers. Yet, the brittleness of these materials has hindered their development. The techniques described herein provide a method for developing novel nano-scale circuitry out of these materials.

Colossal Magnetoresistive (CMR) Materials:

These brittle materials (that are structurally related to the high-Tc superconductors) have received widespread attention over the last decade due to their huge magnetoresistive behavior. By forming nano-scale junctions—which have recently been investigated for their magnetoresistive behavior utilizing CCE—novel spintronic devices can be fabricated using the techniques described herein.

Proposed Theory of Operation (Non-Limiting) of One Embodiment:

Without being bound by any limiting theory of operation, we outline the theory of one embodiment for the formation of parallel nanogaps. In this embodiment, the nanogaps are achieved through a novel arrangement of leads that incorporate electrical shorts close to the location of the desired nanogaps. This novel arrangement is modeled to show that it permits parallel nanogap formation. This theory is extended to a methodology to construct a large array of independent devices that utilizes sacrificial electrical shorts. To this end, a multi-angle evaporation scheme is also formulated to construct the appropriate arrangement of nanogap junctions and electrical shorts. In this scheme, the thermal length sets the maximum density of nanogaps, which can be engineered to make high-density arrays. These processes enable the development of complex molecular-scale circuitry, nanogap arrays for field-emitter displays, and ultra-high resolution detectors and sensors.

Background: Electromigration of a Single Nanogap.

In one embodiment, a single nano-electrode can be approximated well by resistors in series as it is electromigrated to form a nanogap; $R_L$ due to the leads and $R_S$ representing a narrowed constriction where the nanogap forms. As the nanogap forms, $R_S$ increases and the power dissipation in the gap region changes. This causes a temperature change in the region of nanogap formation and leads to a change in the mobility, and thus the electromigration, of metal atoms. Electromigration occurs when a critical power dissipation occurs across the forming nanogap region and can be interpreted as a critical temperature being reached in this region. In order to prevent thermal runaway in the gap forming region, a computer-controlled feedback can be used to actively control the applied voltage across the total resistance, $R_L+R_S$. This feedback monitors the threshold during ramping, defined as Th %=$\Delta R/R$ where R is the measured resistance of the entire circuit. Computer controlled feedback is used to avoid thermal runaway when $R_L>R_S$. At early stages of the electromigration, $R_L$ is typically about 100Ω and $R_S$ about 4Ω so that $R_L>>R_S$ and controlled feedback can prevent thermal runaway.

Unstable Parallel-Electromigration: One View.

Figure 16:
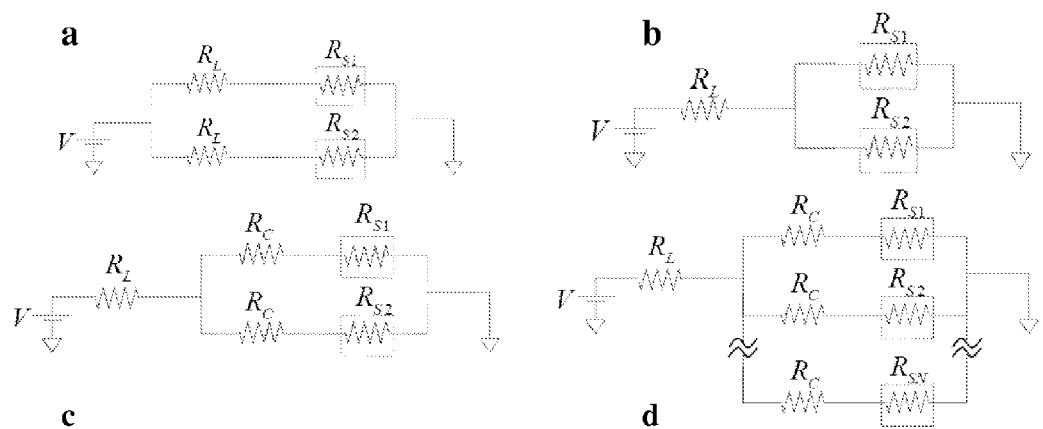
FIG. 16 shows several models for the parallel formation of electromigrated nanogaps; (a) when two nanogap leads are connected far from the gap regions; (b) when two nanogaps are connected on either side with infinitely conducting shorts; (c) a model where the small resistance of the shorts is incorporated; (d) when the model (c) is extended to N nanogaps shorted together in parallel.

Two nanogaps can electromigrate in parallel using the same computer-controlled feedback technique as used for a single junction. In this case the circuit is modeled as shown in FIG. 16$a$, where the gap resistances are $R_{S1}$ and $R_{S2}$, while we have assumed equal lead resistances for the two parallel leads. Using this circuit model we can calculate the power dissipated at each gap, $P_1$ and $P_2$. Since it is difficult to fabricate truly identical initial weak links where the nanogaps will form, one of the junctions will usually be weaker than the other. As we ramp the voltage up across the parallel gaps the weaker junction will therefore begin to electromigrate and increase in resistance. Assuming the weaker junction occurs at lead 1, this will yield an increase in $R_{S1}$. We now ask how the power across each junction changes as $R_{S1}$ increases, which is simply proportional to the partial derivative $\partial P_1/\partial R_{S1}$ and the cross partial derivative $\partial P_2/\partial R_{S1}$. For the circuit of FIG. 16a it can be calculated that $\partial P_1/\partial R_{S1} > \partial P_2/\partial R_{S1}$. This means that the temperature rises faster in the weaker junction as it is electromigrated. This is an unstable scenario for simultaneous nanogap formation and is typically not used for parallel fabrication.

Stable Parallel-Electromigration: a Novel Arrangement with Shorts.

To have stable parallel electromigration the temperature, and also the power dissipation, must rise faster in the stronger of the two junctions while the weaker is electromigrating. Thus, we propose the criterion $$\partial P_1/\partial R_{S1} < \partial P_2/\partial R_{S1}, \quad (1)$$

for stable parallel-electromigration of nanogaps.

If we electrically short the two leads together on either side of the junctions, as in FIG. 16b, we have $$\frac{\partial P_1}{\partial R_{S1}} = V^2 \left\{ -\frac{1}{R_{S1}^2} \cdot \left(\frac{1}{Y+1}\right)^2 + \frac{1}{R_{S1}} \cdot \frac{2R_L}{R_{S1}^2} \cdot \left(\frac{1}{Y+1}\right)^3 \right\}, \quad (2)$$

and $$\frac{\partial P_2}{\partial R_{S1}} = V^2 \left\{ \frac{1}{R_{S2}} \cdot \frac{2R_L}{R_{S1}^2} \cdot \left(\frac{1}{Y+1}\right)^3 \right\}, \quad (3)$$

with $$Y \equiv \frac{R_L}{R_{S1}} + \frac{R_L}{R_{S2}}.$$

Since the first term in Eq. (2) is negative definite, this system will satisfy the stability condition of Eq. (1). As a result, the nanogaps in this arrangement can be electromigrated in parallel.

A more realistic model includes the finite resistances of the shorts, as pictured in FIG. 16c. We find (details not shown) that if the resistance of the shorts is less than the junctions so that, $$R_C < R_S, \quad (4)$$

then the stability condition, Eq. (1), is satisfied. If we extend the model to N junctions in parallel, as pictured in FIG. 16d, we find that Eq. (4) is again the requirement for stable parallel electromigration. Thus, low resistance shorts will permit stable parallel formation through electromigration.

Parallel Electromigration: Scheme for Separating the Nanogaps with Sacrificial Shorts.

Figure 17:
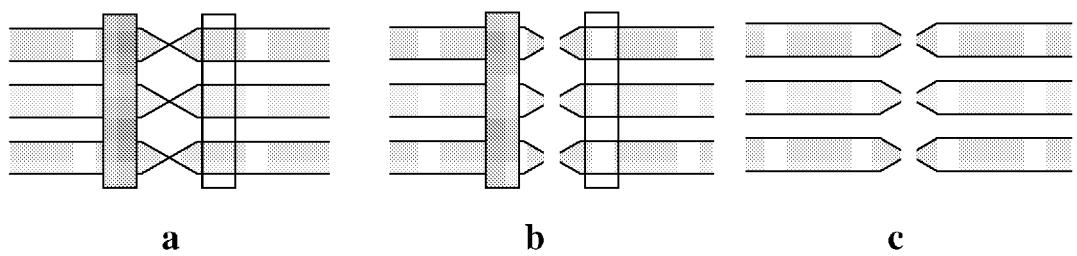
FIG. 17 shows a general scheme for fabricating separate electromigrated nanogaps using sacrificial shorts; two metals are used as in (a) and electromigrated by passing a current from left to right in the structure to yield the nanogaps in (b) then the sacrificial shorts are selectively removed and the nanogaps are electrically isolated.

The use of shorts permits the construction of nanogap arrays. In many applications the nanogaps need to be electrically isolated from one another. Independent nanogap devices can be made by utilizing sacrificial shorts made of materials differing from the main electrode so that they can be selectively etched or oxidized away after the parallel electromigration. A schematic of this method is represented in FIG. 17.

Parallel Electromigration: Method to Fabricate Separated Nanogaps Using Multi-Angle Evaporation.

Figure 18:
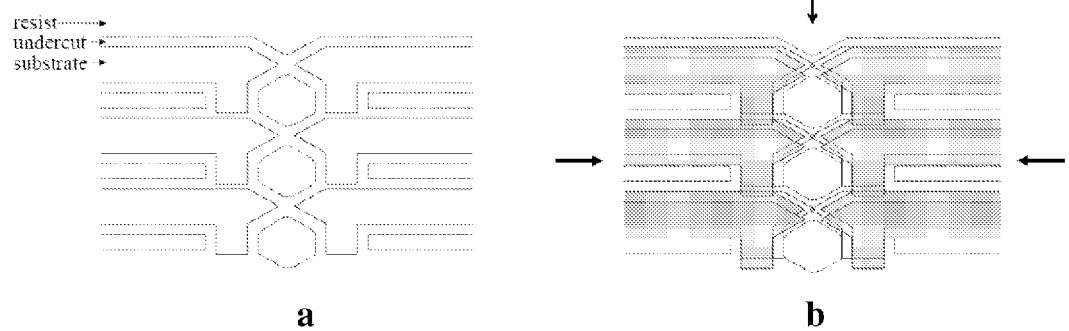
FIG. 18 shows a schematic for proposed method to fabricate an array of separated nanogap leads for application in complex circuitry (a) shows the resist pattern looking towards the surface of the substrate; regions within solid lines have no resist, while regions between solid and dashed lines have overhanging resist; (b) shows the results of four angle evaporations: the first two are thin layers of metal A angled towards the left and right arrows, the third is a thick layer normal to the page of metal A, while the last is angled down of metal B; after electromigration of nanogaps in parallel, only the metal B is removed with selective etching or oxidation—leaving separate nanogaps.

A method we propose to fabricate the junctions and sacrificial shorts is illustrated in FIG. 18. This is a method to fabricate parallel nanogaps shorted together with sacrificial shorts using multi-angle evaporation through a shadow mask that avoids covering the nanogap regions. The method comprises (1) the deposition of the leads with weak junctions and (2) the deposition of sacrificial shorts at a different angle so as to avoid covering the nanogap region. To this end, a resist layer is first spin coated onto a supporting substrate and either an electron beam or light is exposed within the solid-line pattern of FIG. 18a. (denoted by "substrate"). In these regions, the resist can be easily removed down to the substrate surface with the appropriate solvent, whereas in regions far from these areas the resist is not dissolved. Near the exposed areas there is an overhanging portion of resist between the dashed and solid lines (denoted by "undercut") formed from the backscattering of radiation off the surface of the substrate. After this, four evaporation steps using two metals (A and B) permits the construction of the shunted junctions. The first two evaporations are thin layers of the metal A made at angles between the normal to the page and the right and left arrows in FIG. 18b. A third, thick, evaporation normal to the surface of metal A followed by an evaporation of metal B at angle between the normal and the arrow pointing down in the FIG. 18b constructs the low-resistance shunts. At this point the remaining resist can be lifted off and the junctions electromigrated in parallel. After electromigration, the shunts constructed with metal B can be oxidized or etched away with a solution which does not attack metal A—leaving an array of electrically separated nanogap junctions.

Parallel Electromigration: Increasing the Density by Engineering Large Temperature Gradients.

For use in complex circuits, it is also desirable to construct as dense an array of nanogaps as possible. Since the formation of electromigrated nanogaps is strongly tied to the local temperature rise due to the applied current,[3] we propose that the local heating length, $\xi_T$, will determine the minimum spacing (and thus the highest density) of nanogap junctions. Within a radius of roughly $\xi_T$ from the weak link junction of each lead the temperature will rise appreciably above the ambient temperature of the environment. If two junctions are spaced much closer than this length, we expect that a single nanogap will form instead of the intended separate gaps. By constructing the initial wires to promote large temperature gradients near the junctions, so that $\xi_T$ is as small as possible, one should be able to engineer higher density arrays of nanogaps. Current experiments suggest that $\xi_T$ can be as small as 20 nm under certain conditions, and we expect that this could possibly be engineered to become several times smaller still.

Stage of Development: Experimental Evidence of Parallel Electromigration.

Figure 19:
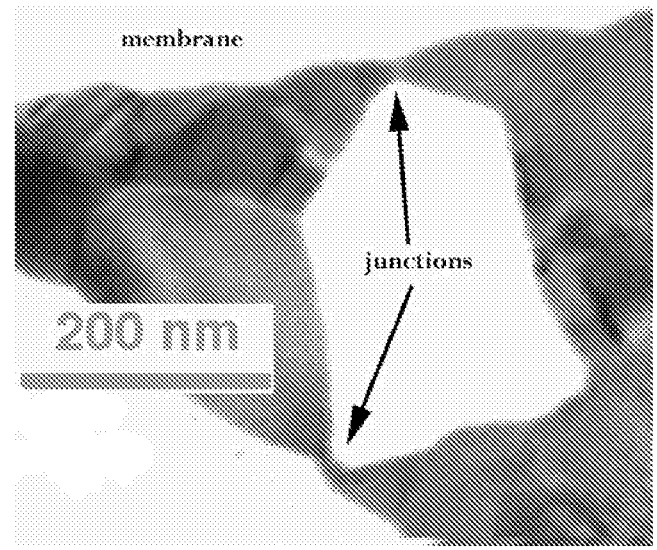
FIG. 19 shows two parallel Au junctions (with Au appearing as dark regions) that are being electromigrated with a current applied from left to right; the Au leads are supported on a transparent membrane which is not visible; the close connection of the two junctions acts as if a short is placed on either side of them, as in the schematic of FIG. 16*b;*
Figure 20:
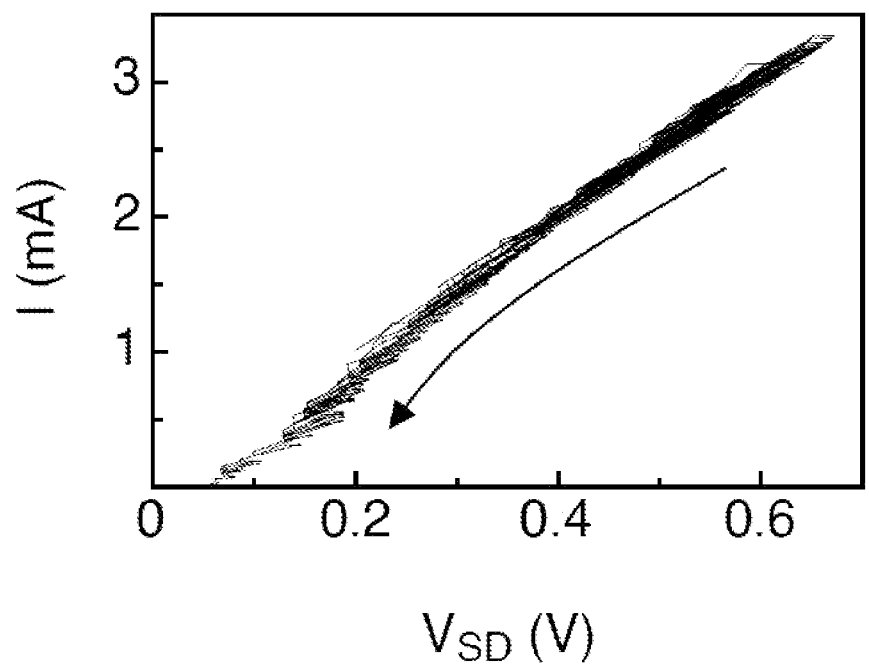
FIG. 20 shows parallel formation of the two nanogaps that are shorted together in FIG. 19.
Figure 21:
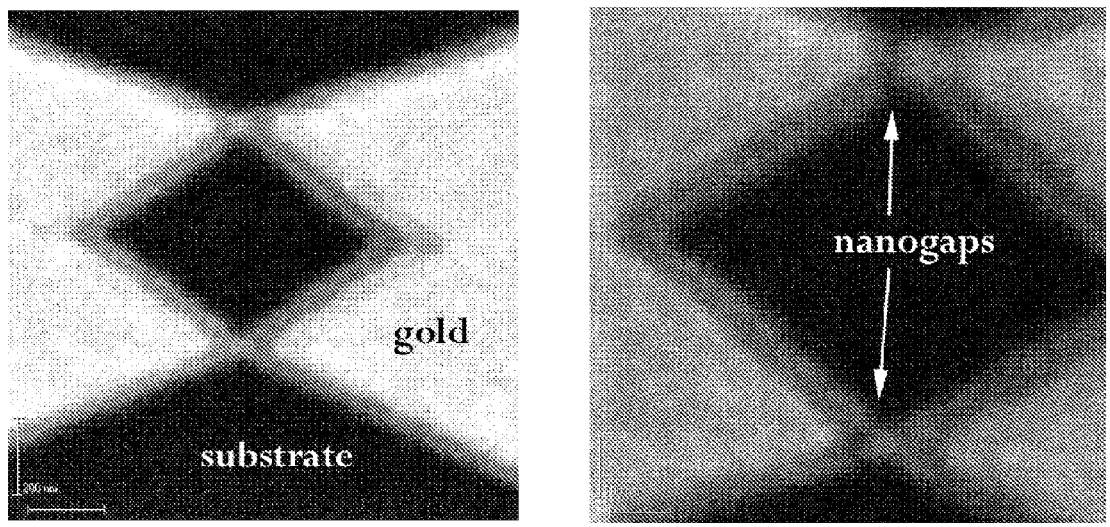
FIG. 21 shows before (a) and after (b) of parallel electromigration performed on two gold junctions; the current is applied from left to right, and since this is a scanning electron micrograph the white areas are gold, while the dark areas are substrate; the initial structure is formed in a multiple angle evaporation technique using a shadow mask; two nanogap junctions are clearly visible in (b) after the parallel electromigration.

Parallel electromigration of two nanogap junctions is demonstrated. A sample comprises two weak-link junctions on a $SiN_x$ nitride membrane shown in FIG. 19 and labeled as "junctions." The dark regions in FIG. 19 are the deposited Au, while the white regions are the supporting transparent membrane. FIG. 20 shows the controlled electromigration of the two gaps in unison using an applied current (which is applied from left to right) to the structure in FIG. 19. This demonstrates that we are able to electromigrate two nanogaps simultaneously. The electrode design can be further modified to improve the parallel electromigration and to increase the number of nanogaps that can electromigrate in parallel. To this end, we have recently fabricated a pair of initial gold junctions on an $SiO_2$ substrate using multi-angle evaporation through a shadow mask, shown in FIG. 21a. After parallel controlled electromigration, we have clearly fabricated two separate nanogaps, as seen in FIG. 21b.

Applications.

In addition to complex nano-electronic circuits, other possible applications for a nanogap array include uses in novel displays, detectors, and imaging devices with unsurpassed resolution. This includes the illumination of a phosphor coated screen to emit light in a television display, next generation vacuum tube amplification and computation, and the generation of X-rays in imaging technologies. One major advantage of the nanogap arrays described herein stems from the fact that as the width of a nanogaps is made smaller and the density of nanogap arrays increases, the voltage required to scatter tunneling electrons for display applications decreases. Since our nanogap arrays can employ a controlled electromigration technique, the system is readily optimized to reduce power consumption. The nanogap arrays described herein will enable low-power computer and television displays.

Alternative Methods to Fabricate Nanogap Arrays
Alternative Lithography Processing Technique.

Figure 22:
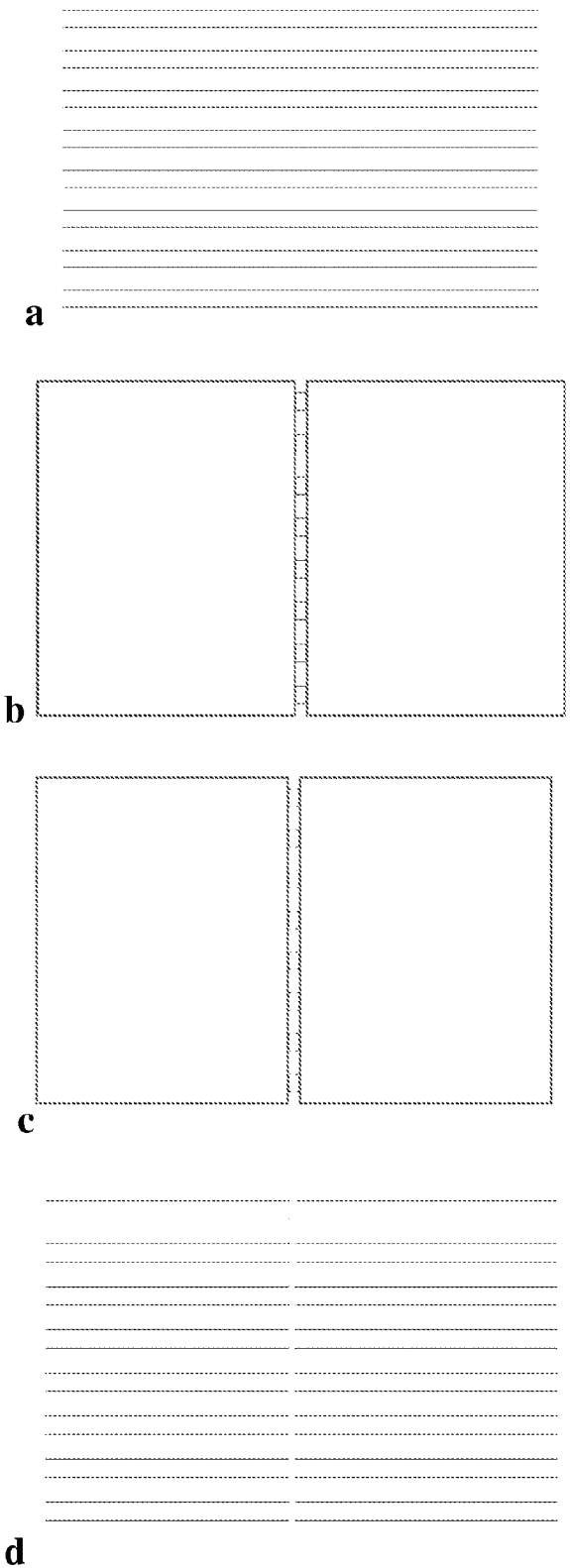
FIG. 22 shows (a) Parallel leads of metal A are fabricated with lithography; (b) the leads are covered by two large pads made of metal B; (c) The array is electromigrated to form a series of nanogaps; (d) By selective etching of metal B, separate leads with well positioned nanogaps are produced.

An alternative method is provided for achieving a device capable of achieving a nanogap array in comparison to the methods discussed above. Parallel narrow thin metallic leads (made from metal A, such as Au) are fabricated on top of an insulating substrate, as shown in FIG. 22(a). These leads can be about 100 nm wide or narrower, and thinner than 50 nm. Using lithography of a second metal (B), such as Cr, place two large thick pads on top of the entire structure. This will short all the wires together, as shown in FIG. 22(b). The distance between these two large wires should be as small as possible so that the resistance of the short metal leads of A are less than the interjunction resistances of metal B. At this point the self balancing parallel electromigration can be performed to achieve the array of nanogaps in FIG. 22(c). Using a selective etchant that etches only metal B, we can be left with the leads shown in FIG. 22(d).

Alternative Method Based on Stressing the Initial Nanowires.

A method for controlling individual nanogaps has been achieved by stressing long nano-scale wires, according to F. O. Hadeed, and C. Durkin, Appl. Phys. Lett. 91, 123120 (2007). This technique can be extended to achieve parallel balanced formation of nanogaps over a limited range. The improved techniques relies on the fact that significant stress is built up in a long wire carrying an electric current due to electromigration forces and the variation of thermal expansion throughout the wire due to joule heating. This stress causes a catastrophic tear in the long nanowire which will induce a void to form in the wire. As the void forms, the temperature profile within the wire rapidly changes and the systems switches over to the constant power regime. If the initial wire is long enough, the applied voltage required to tear the wire with the induced stress can be very low. This prevents the system from experiencing thermal runaway and results in a stable, partially electromigrated constriction that can be described by the constant power model. As the long initial wire could contain the entire voltage drop from the voltage source, self-balancing will then proceed after the long wire is torn.

Figure 23:
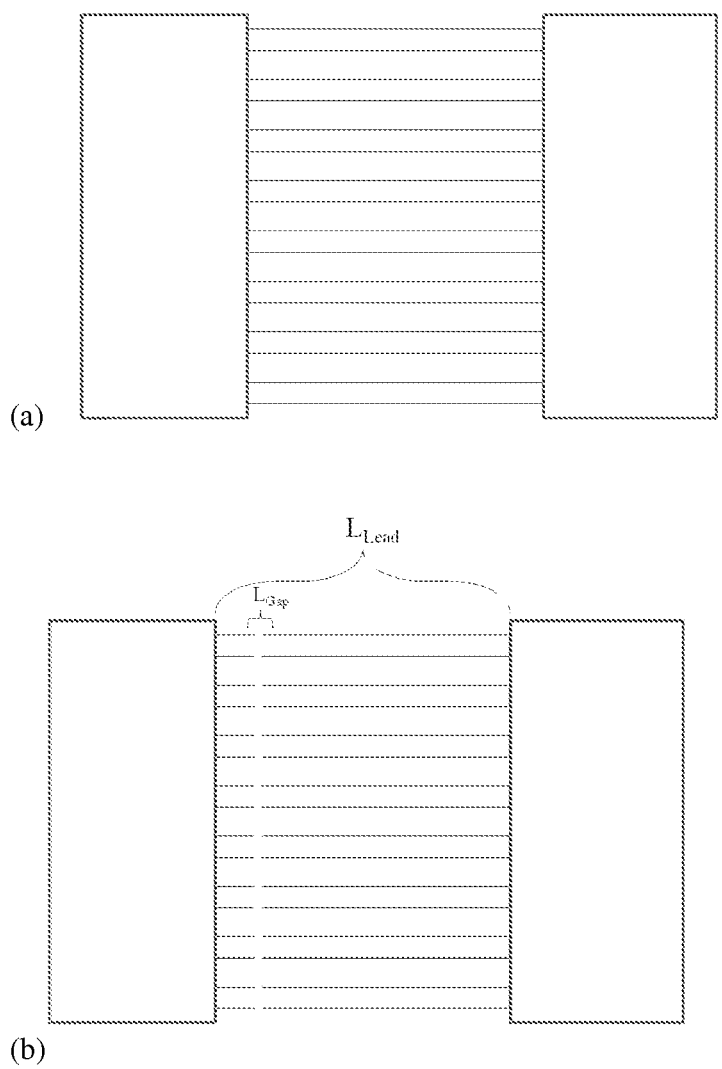
FIG. 23 shows (a) long nano-wires (of metal A) are shorted together with a different metal B; (b) the metals are stressed due to electromigration and joule heating which partially tears the wires at one end; if the resistance of the entire lead plus the electrical shorts is less than the partially torn region, then parallel self-balanced electromigration can be achieved to form nanogaps at the locations of the partial tears.

This stressing technique can also be extended to the parallel formation of nanogaps, as shown in FIG. 23. First, long nano-wires (of metal A) are shorted together with a different metal B. Then the long leads are stressed due to electromigration and joule heating which partially tears the wires at one end. If the resistance of the entire lead plus the electrical shorts is less than the partially torn region, then parallel self balanced electromigration can be achieved to form nanogaps at the locations of the partial tears. The length of the initial lead ($L_{Lead}$) is chosen to achieve this and depends on the tear size ($L_{Gap}$). The two large metallic shorts at the ends can then be selectively etched to achieve an array of separated nanogaps.

Using a Feedback Amplifier in the Controlled Feedback Technique with Parallel Electromigration.

Recently, another new technique has emerged whereby feedback from an amplifier is incorporated into the circuitry in order to control the formation of a single nanogap. The circuit essentially keeps the voltage fixed across the nanogap by using two nearby sensing leads which sink negligible current and connecting them to a potentiostat. This technique can also be directly applied to the self-balancing array of nanogaps by utilizing two voltage leads on either side of the array, as close as possible to the nanogaps.

What is claimed is:

1. A method for fabricating a plurality of nanogaps, comprising:
controllably applying a voltage simultaneously across a plurality of constrictions residing in a first conductive material comprising a plurality of ions,
the constrictions being placed in parallel electrical communication with one another by a second conductive material,
the electrical resistance between neighboring constrictions being less than the electrical resistance across a constriction,
the controllably applied voltage giving rise to heating within the constrictions, thereby forming the plurality of nanogaps simultaneously,
the heating within the constrictions giving rise to the essentially simultaneous formation of the plurality of nanogaps upon application of the voltage, each nanogap comprising two opposing faces, each face of the opposing electrodes being essentially crystalline, and
the mean separation distance between the opposing faces of the nanogaps is in a range of from about 0.1 nm less than 5 nm.

2. The method of claim 1, wherein the faces of the nanogaps are essentially crystalline.

3. The method of claim 1, wherein the first conductive material comprises a substance nonreactive to air, a noble metal, an oxide conductor, a high-superconducting temperature superconductor, a colossal magnetic resistive oxide, an inert alloy, graphene, a multi-walled nanotube, or any combination thereof.

4. The method of claim 1, wherein the second conductive material comprises chromium, aluminum, or a combination thereof.

5. The method of claim 3, wherein the noble metal comprises gold, platinum, palladium, rhodium, ruthenium, iridium, osmium or any combination thereof.

6. The method of claim 1, wherein a constriction comprises at least one narrowed region.

7. The method of claim 6, wherein the narrowed regions of the constrictions are separated from one another by an average distance of at least about 50 nm.

8. The method of claim 6, wherein the at least one narrowed region comprises a characteristic width of less than about 100 nm.

9. The method of claim 1, wherein two or more constrictions are oriented essentially parallel to one another.

10. The method of claim 1, wherein the voltage is controllably applied at about ambient temperature.

11. The method of claim 1, wherein the applied voltage is in the range of from about 0.2 V to about 2 V per constriction.

12. The method of claim 1, wherein controllably applying the voltage comprises increasing the applied voltage until the conductance value of the conductive material changes.

13. The method of claim 1, wherein the heating gives rise to electromigration of at least a portion of the ions of the conductive material residing at the narrowed regions of the constrictions.

14. The method of claim 1, wherein at least a portion of the second conductive material placing two or more nanogaps in electrical communication is removed, transformed, or both.

15. A device produced by the method of claim 14, wherein the separation distance between opposing electrodes of any nanogap varies by less than 0.3 nm from the mean opposing electrode separation of the plurality of nanogaps.

16. The method of claim 1, wherein at least two nanogaps form essentially simultaneously following the application of the applied voltage.

17. The method of claim 1, wherein the separation distance between opposing faces of any one nanogaps varies by less than 0.3 nm from the mean separation distance of the plurality of nanogaps.

18. A device, comprising:
   a plurality of nanogaps formed by simultaneous resistive heating in a first conductive material,
   the nanogaps comprising opposing electrodes,
   the opposing electrodes being separated by less than about 5 nm,
   the opposing electrodes comprising faces, and
   the faces of the opposing electrodes being essentially crystalline;
   wherein the separation distance between opposing electrodes of any nanogap varies by less than 0.3 nm from the mean opposing electrode separation of the plurality of nanogaps.

19. The device of claim 18, wherein the first conductive material comprises a substance nonreactive to air, a noble metal, an oxide conductor, a high-Tc superconductor, a colossal magnetic resistive oxide, an inert alloy, graphene, a multi-walled nanotube, or any combination thereof.

20. The device of claim 18, wherein a second conducting material places two or more nanogaps in electrical communication with one another.

21. The device of claim 18, further comprising one or more molecules residing within one or more nanogaps.

22. The device of claim 18, wherein one or more of the nanogaps is individually electrically addressable.

* * * * *